US012678284B2

(12) United States Patent
Conklin et al.

(10) Patent No.: US 12,678,284 B2
(45) Date of Patent: Jul. 14, 2026

(54) ADJUSTABLE ANNULOPLASTY RING AND DELIVERY SYSTEM

(71) Applicant: Edwards Lifesciences Corporation, Irvine, CA (US)

(72) Inventors: Brian S. Conklin, Orange, CA (US); Amy E. Munnelly, Irvine, CA (US); Milton Deherrera, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 757 days.

(21) Appl. No.: 18/159,982

(22) Filed: Jan. 26, 2023

(65) Prior Publication Data

US 2023/0165681 A1    Jun. 1, 2023

Related U.S. Application Data

(63) Continuation of application No. PCT/US2021/042056, filed on Jul. 16, 2021.

(60) Provisional application No. 63/059,080, filed on Jul. 30, 2020.

(51) Int. Cl.
A61F 2/24        (2006.01)

(52) U.S. Cl.
CPC .......... A61F 2/2448 (2013.01); A61F 2/2433 (2013.01); A61F 2/2445 (2013.01); A61F 2/2466 (2013.01); *A61F 2250/0004* (2013.01)

(58) Field of Classification Search
CPC .... A61F 2/2448; A61F 2/2445; A61F 2/2442; A61F 2250/0004
See application file for complete search history.

(56) References Cited

U.S. PATENT DOCUMENTS

| 1,250,153 A | 12/1917 | Ellis |
| 4,042,979 A | 8/1977 | Angell |
| 4,290,151 A | 9/1981 | Massana |

(Continued)

FOREIGN PATENT DOCUMENTS

| CN | 104000671 A | * | 8/2014 | .......... A61F 2/2448 |
| CN | 114452039 A | * | 5/2022 | .......... A61F 2/2442 |

(Continued)

OTHER PUBLICATIONS

Bouleti, MD, C., et al. "Transfemoral Tricuspid Valve-in-Ring Implantation Using the Edwards Sapien XT Valve, One-Year Follow-Up," Cardiovascular Interventions. 2015;8.

*Primary Examiner* — Alvin J Stewart
(74) *Attorney, Agent, or Firm* — Guy Cumberbatch

(57)        ABSTRACT

An annuloplasty ring for repair of mitral and tricuspid valves that can be shape adjusted once installed to fine-tune the shape and correct for small errors in the inherently imprecise sizing process. The ring has an adjustable 3D ring core of malleable metal that can be reshaped in real-time during the procedure before or after the patient is weaned off-pump by applying simple displacements to a cable and housing arrangement. The shape of the annuloplasty ring is adjusted incrementally in steps until an optimum level of regurgitation reduction is attained. Once the surgeon is satisfied with the result, the delivery system can be can easily detached from the implant and removed. The thickness of the core could be continuously variable to control how and where deformation occurs. The ring may also incorporate an expansion joint to enable a subsequent valve-in-ring procedure.

26 Claims, 19 Drawing Sheets

(56)                References Cited

U.S. PATENT DOCUMENTS

| | | | | |
|---|---|---|---|---|
| 5,104,407 | A * | 4/1992 | Lam | A61F 2/2448 |
| | | | | 623/2.36 |
| 5,201,880 | A | 4/1993 | Wright et al. | |
| 5,593,435 | A | 1/1997 | Carpentier et al. | |
| 5,607,471 | A | 3/1997 | Seguin et al. | |
| 5,674,279 | A | 10/1997 | Wright et al. | |
| 5,814,098 | A | 9/1998 | Hinnenkamp et al. | |
| 5,855,601 | A | 1/1999 | Bessler et al. | |
| 5,885,228 | A | 3/1999 | Rosenman et al. | |
| 5,972,030 | A | 10/1999 | Garrison et al. | |
| 6,210,432 | B1 | 4/2001 | Solem et al. | |
| 6,231,601 | B1 | 5/2001 | Myers et al. | |
| 6,419,696 | B1 | 7/2002 | Ortiz et al. | |
| 6,524,338 | B1 | 2/2003 | Gundry | |
| 6,602,288 | B1 | 8/2003 | Cosgrove et al. | |
| 6,689,164 | B1 | 2/2004 | Seguin | |
| 6,726,716 | B2 | 4/2004 | Marquez | |
| 6,881,220 | B2 | 4/2005 | Edwin et al. | |
| 7,063,722 | B2 | 6/2006 | Marquez | |
| 7,455,690 | B2 | 11/2008 | Cartledge et al. | |
| 7,951,196 | B2 * | 5/2011 | McCarthy | A61F 2/2445 |
| | | | | 623/2.37 |
| 7,993,395 | B2 * | 8/2011 | Vanermen | A61B 5/1076 |
| | | | | 623/2.37 |
| 9,265,608 | B2 | 2/2016 | Miller et al. | |
| 9,937,041 | B2 * | 4/2018 | Carpentier | A61F 2/2448 |
| 10,039,531 | B2 * | 8/2018 | Yoganathan | A61B 17/00234 |
| 10,631,983 | B1 * | 4/2020 | Christianson | A61F 2/2436 |
| 12,514,705 | B2 * | 1/2026 | Skarsgard | A61F 2/2445 |
| 2003/0130731 | A1 | 7/2003 | Vidlund et al. | |
| 2004/0006384 | A1 * | 1/2004 | McCarthy | A61F 2/2448 |
| | | | | 623/2.37 |
| 2004/0122516 | A1 * | 6/2004 | Fogarty | A61F 2/2409 |
| | | | | 623/2.37 |
| 2004/0148021 | A1 | 7/2004 | Cartledge et al. | |
| 2004/0153144 | A1 | 8/2004 | Seguin | |
| 2005/0004668 | A1 * | 1/2005 | Aklog | A61F 2/2448 |
| | | | | 623/2.36 |
| 2005/0060030 | A1 | 3/2005 | Lashinski et al. | |
| 2005/0192666 | A1 * | 9/2005 | McCarthy | A61F 2/2445 |
| | | | | 623/2.36 |
| 2005/0283232 | A1 | 12/2005 | Gabbay | |
| 2007/0016287 | A1 | 1/2007 | Cartledge et al. | |
| 2007/0083259 | A1 * | 4/2007 | Bloom | A61F 2/2454 |
| | | | | 623/2.37 |
| 2007/0112424 | A1 | 5/2007 | Spence et al. | |
| 2007/0213582 | A1 * | 9/2007 | Zollinger | A61B 17/0401 |
| | | | | 600/37 |
| 2009/0292353 | A1 * | 11/2009 | Yoganathan | A61F 2/2454 |
| | | | | 623/2.11 |
| 2010/0023117 | A1 | 1/2010 | Yoganathan et al. | |
| 2010/0063586 | A1 | 3/2010 | Hasenkam et al. | |
| 2010/0152845 | A1 * | 6/2010 | Bloom | A61F 2/2454 |
| | | | | 623/2.37 |
| 2010/0174365 | A1 * | 7/2010 | Parravicini | A61F 2/2448 |
| | | | | 623/2.36 |
| 2010/0318184 | A1 | 12/2010 | Spence | |
| 2012/0203330 | A1 | 8/2012 | Cartledge et al. | |
| 2014/0081393 | A1 | 3/2014 | Hasenkam et al. | |
| 2016/0317289 | A1 * | 11/2016 | Tozzi | A61F 2/2451 |
| 2017/0281337 | A1 | 10/2017 | Campbell | |
| 2020/0170799 | A1 | 6/2020 | Yellin et al. | |
| 2022/0096232 | A1 * | 3/2022 | Skaro | A61F 2/2445 |
| 2023/0165681 | A1 * | 6/2023 | Conklin | A61F 2/2466 |
| | | | | 623/2.37 |
| 2023/0414355 | A1 * | 12/2023 | Conklin | A61F 2/2448 |
| 2026/0033949 | A1 * | 2/2026 | Jiang | A61F 2/2436 |

FOREIGN PATENT DOCUMENTS

| | | | | |
|---|---|---|---|---|
| CN | 115835836 A * | 3/2023 | | A61F 2/2448 |
| EP | 2531115 A2 | 12/2012 | | |
| WO | 2009052397 A1 | 4/2009 | | |
| WO | 2009137805 A1 | 11/2009 | | |
| WO | WO-2015058808 A1 * | 4/2015 | | A61F 2/2445 |
| WO | WO-2022192572 A1 * | 9/2022 | | A61F 2/2466 |

* cited by examiner

No Anterior kinking

Posterior kinking

Less posterior kinking

Very little posterior kinking

40'

-0.54 mm

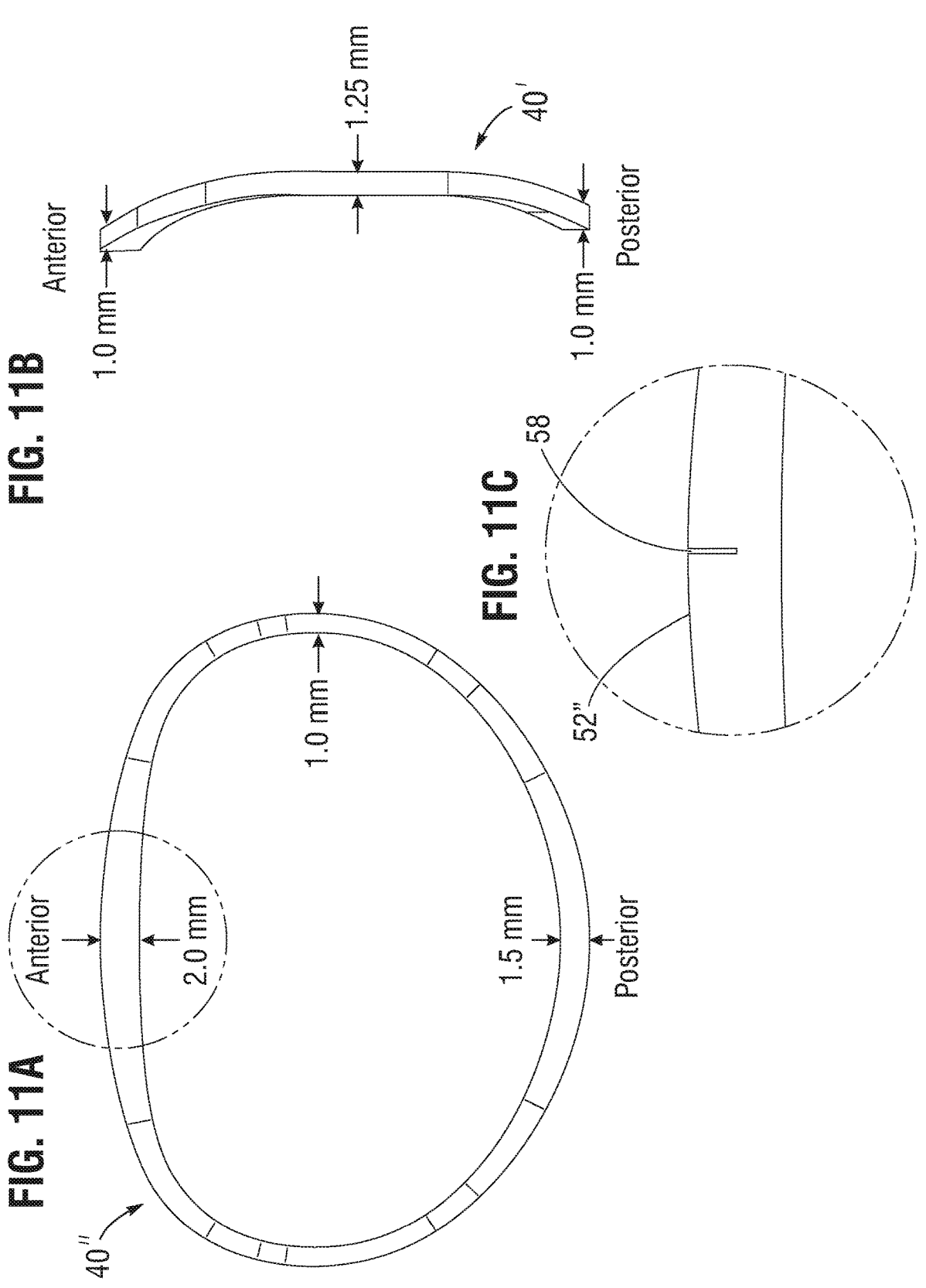

+0.096 mm

ADJUSTABLE ANNULOPLASTY RING AND DELIVERY SYSTEM

This application is a continuation of International Patent Application No. PCT/US21/42056, filed Jul. 16, 2021, which claims the benefit of U.S. Patent Application No. 63/059,080, filed Jul. 30, 2020, the entire disclosures all of which are incorporated by reference for all purposes.

TECHNICAL FIELD

The present application relates generally to annuloplasty rings, and in particular to an adjustable mitral or tricuspid annuloplasty ring and delivery system.

BACKGROUND

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice. The mitral and tricuspid valves are defined by fibrous rings of collagen, each called an annulus, which forms a part of the fibrous skeleton of the heart. The annulus provides peripheral attachments for the two cusps or leaflets of the mitral valve (called the anterior and posterior cusps) and the three cusps or leaflets of the tricuspid valve. The native valve leaflets flex outward when the valve opens and their free edges come together or coapt in closure.

Various surgical techniques may be used to repair a diseased or damaged valve. A commonly used repair technique effective in treating incompetence is annuloplasty, which often involves reshaping or remodeling the annulus by attaching a prosthetic annuloplasty repair segment or ring thereto. For instance, the goal of a posterior mitral annulus repair is to bring the posterior mitral leaflet forward toward to the anterior leaflet to better allow coaptation. The annuloplasty ring is designed to support the functional changes that occur during the cardiac cycle: maintaining coaptation and valve integrity to prevent reverse flow while permitting good hemodynamics during forward flow.

Annuloplasty rings may be stiff, flexible or semi-rigid, and a "remodeling" annuloplasty ring typically has an inner core that resists conforming to the native annulus shape and instead forces the annulus to conform to it. Remodeling annuloplasty bands or rings are "generally rigid" or "semi-rigid" in that they will resist distortion when subjected to the stress imparted thereon by the mitral valve annulus of an operating human heart. In this sense, "distortion" means substantial permanent deformation from a predetermined or manufactured shape (e.g., the ring or ring will tend to return to its preset shape in use). A typical remodeling annuloplasty ring comprises an inner substrate or core of a metal such as a rod or multiple bands of stainless steel or titanium covered with a biocompatible fabric or cloth and perhaps silicone to allow the ring to be sutured to the fibrous annulus tissue.

Annuloplasty rings may have a variety of shapes in plan view, including closed or continuous oval, circular, rounded D-shaped, or kidney-shaped, and open or discontinuous C-shaped, sometimes referred to as a band. Examples are seen in U.S. Pat. Nos. 5,041,130, 5,104,407, 5,201,880, 5,258,021, 5,607,471 and, 6,187,040. Most rigid and semi-rigid annular rings for the mitral valve have a kidney-like or D shape, with a curved posterior segment co-extensive with the posterior valve leaflet, and a somewhat straighter anterior segment co-extensive with the anterior valve leaflet. One popular annuloplasty ring is the partially flexible Carpentier-Edwards PHYSIO® ring available from Edwards Lifesciences of Irvine, CA The Physio® ring is a closed "semi-rigid" ring because it offers selective flexibility at the posterior section while preserving the remodeling effect through a rigid anterior section. The newer PHYSIO II® ring from Edwards Lifesciences also features up and down curves to better fit the nonplanar contours of the mitral annulus. Various other rings have posterior bows, e.g., U.S. Pat. Nos. 6,805,710 and 6,858,039, 7,959,673, or other three-dimensional configurations.

Currently, during a mitral valve repair procedure, the size of the annuloplasty device to be implanted is determined by comparing different sizer templates to the patient's anatomy until the surgeon determines which one looks correct based on, for example, anterior leaflet area or length, inter-commissural distance, and so on. However, unlike for an aortic valve replacement, where the goal is to implant the largest valve that will safely fit the patient's anatomy, for mitral repair procedures the goal is often to implant a repair device that is somewhat smaller than the annulus, thus reducing the perimeter, or, more importantly, the anterior-posterior diameter, of the valve and restoring coaptation. The surgeon must make an "educated guess" as to how much reduction in size is appropriate for any given patient and their specific disease state. If the wrong size repair product is chosen, the result may be a poor outcome manifested by residual mitral regurgitation (MR), insufficient coaptation length, high pressure gradients, or systolic anterior motion (SAM). If any of these conditions are found once the patient is weaned off-pump, the surgeon must make the difficult decision of going back on pump, with its associated morbidity and mortality, or leaving the patient with a sub-optimal repair, and its associated sequalae.

In attempts to optimize the shape of the repair device, adjustable annuloplasty devices such as the CARDIOBAND® mitral repair device are available from Edwards Lifesciences Corp. of Irvine, CA Modern annuloplasty rings such as the Edwards PHYSIO II® ring have a very specific 3-dimensional shape, which has been shown to be important in maintaining and restoring anatomy as well as minimizing leaflet stresses. Adjustable devices have yet to successfully combine orifice downsizing with three-dimensional remodeling.

Despite numerous designs presently available or proposed in the past, there is a need for an annuloplasty ring that may be shaped adjusted to effect repair of the malfunctioning valve while avoiding negative outcomes.

SUMMARY

The present disclosure provides an annuloplasty ring for repair of mitral and tricuspid valves, through both traditional surgical exposures as well as minimally invasive approaches. Present application discloses an annuloplasty device that can be adjusted once the patient is weaned off-pump in order to fine-tune the anterior-posterior (AP) diameter of the mitral valve in order to correct for small errors in the inherently imprecise sizing process. Such a ring has the potential to reduce poor mitral valve repair outcomes and the need to go back on-pump in many cases. Once adjustments are made, the delivery system attachments can be disengaged, leaving the patient with a customized annuloplasty device tailored to their specific anatomy.

The disclosed ring has an adjustable 3D ring core and delivery system. The system uses a malleable metal core that can be reshaped in real-time during the procedure before or after the patient is weaned off-pump by applying simple displacements to a cable and housing arrangement via a delivery system. Once the surgeon is satisfied with the result, they can easily detach the delivery system from the implant and finish closing the patient. The disclosed system is simple to manufacture and has the added benefit of a true 3D annuloplasty ring shape.

The core of the ring is an implantable elastic-plastic malleable metal, such as annealed stainless steel or titanium alloy. An initial in-plane shape could be similar to an Edwards Physio II® ring, preferably with a 3D saddle shape. The thickness of the core could be continuously variable to control how and where deformation occurs. As will be seen, the anterior aspect of the ring core could be thicker, which preferentially causes shape changes to occur in the posterior region. The delivery system consists of a handle (not shown) with an attached cable housing and an attached reshaping cable, the displacement of which can be changed relative to the delivery system handle and cable housing via a control on the handle such as a dial or slide. The cable housing terminates at its distal end at a cable housing boss on the anterior side of the ring core. The cable housing is detachably connected to the cable housing boss using a threaded connection or some other means. The reshaping cable runs through the cable housing and on its distal end extends out of the cable housing and cable housing boss and is detachably connected to the cable boss on the posterior side of the ring core.

One example of an adjustable annuloplasty ring and delivery system comprises an annuloplasty ring having a continuous peripheral shape around a central aperture, the annuloplasty ring having an inner core formed of an elastic-plastic metal having a yield strength and a suture-permeable interface surrounding the inner core and extending around the peripheral shape. A delivery system has a flexible sheath coupled to the inner core at a first side of the annuloplasty ring, the sheath housing a flexible cable configured to slide through the sheath. The cable passes through the first side of the annuloplasty ring and extends across the central aperture to a diametrically-opposed second side of the annuloplasty ring, whereby the cable attaches securely to the inner core at the second side. An actuation mechanism at a proximal handle of the delivery system is configured to pull the cable proximally relative to the sheath, and the inner core has cross-sectional dimensions and the yield strength being such that a dimension between the first and second sides is permanently reduced by a predetermined tension on the cable.

The annuloplasty ring may be shaped for implant at the mitral annulus and the peripheral shape is a rounded D-shape with a relatively straight anterior segment opposite an arcuate posterior segment, with a shorter minor axis extending between the anterior and posterior segments and a longer major axis extending perpendicular to the minor axis and between side segments, and wherein the first side is the anterior segment and the second side is the posterior segment. The inner core may have a radial thickness in the anterior segment that is greater than a radial thickness in the posterior segment. Preferably, the inner core has an axial thickness in the side segments that is greater than axial thicknesses in both the anterior and the posterior segments.

The elastic-plastic metal may have a yield strength less than about 300 MPa, and is preferably a titanium alloy. The inner core may have a rectangular cross-sectional shape.

Optionally, the inner core has at least one expansion joint around the peripheral shape which permits expansion of the inner core upon application of a dilatory force greater than normal physiological forces imparted to the inner core from a surrounding annulus. In one example there are two expansion joints.

The sheath and cable may form a primary shape adjustment mechanism, and the delivery system may further include a secondary shape adjustment mechanism including a flexible second sheath with a second cable configured to slide through the second sheath. The second cable passes through a third side of the annuloplasty ring and extends across the central aperture to a diametrically-opposed fourth side of the annuloplasty ring, whereby the second cable attaches securely to the ring core at the fourth side, and wherein the first cable and second cable cross the central aperture at about a 90° angle with respect to each other.

The inner core desirably has a rectangular cross-sectional shape and is radially thicker in the first side than in the second side, and the peripheral shape is three-dimensional forming a saddle with the first and second sides bowed upward from intermediate segments therebetween, and wherein the inner core is axially thicker in the intermediate segments that it is in the first and second sides.

Another example of the present application is a method of implanting and adjusting the size of any of the annuloplasty rings disclosed herein. First, an annuloplasty ring is advanced along an array of anchoring sutures into contact with the target annulus, and the sutures tied off. Access incisions are sealed around a sheath of shape adjustment mechanism integrated with the ring and the patient is removed from bypass so that the normal functioning of the heart can be restarted. Echocardiography or other visualization technique can be used to determine the effect of the ring installation on regurgitation. If any regurgitation is detected, the clinician makes an initial shape adjustment of the annuloplasty ring and determines if the regurgitation is reduced. The shape of the annuloplasty ring is adjusted incrementally in steps until an optimum level of regurgitation reduction is attained. That is, a first incremental constricting force is applied to reduce the ring size. When the first incremental constricting force is removed the material of the ring core springs backward but not all of the way due to residual deformation. Thus, for example, during the first application of force the ring core experiences an AP diameter change of about 2 mm, but then the ring core springs back so that the final deformation is only about 1 mm. After the application of a second incremental constricting force, the ring core experiences a similar AP diameter change that increases from about 1 mm to about 3 mm from the original diameter, but then again springs back to about 2 mm after the force is removed. This step-wise deformation of the ring core continues and permits a clinician to test out a particular deformation without committing to it. There is thus a ratcheting effect that will allow the surgeon to test a particular amount of shape change before committing to it. Subsequently, the shape adjustment mechanism is decoupled from the ring and removed from the body.

A second method for implanting and adjusting the size of an annuloplasty ring at a native annulus of a simulated patient comprises first pre-installing an array of anchoring sutures at a native annulus. An annuloplasty ring is advanced using a delivery system along the array of anchoring sutures and into contact with the native annulus. The annuloplasty ring has a continuous periphery and an elastic-plastic metallic core and the delivery system includes a delivery sheath with a distal end engaged with a first side of the annuloplasty ring. The delivery system further includes an elongated flexible cable extending through a lumen and passing through the first side of the annuloplasty ring and across a central orifice to engage a second side thereof. The method includes the steps of:

anchoring the annuloplasty ring to the native annulus with the anchoring sutures;

ensuring the heart is beating;

viewing blood flow through the annuloplasty ring anchored at the native annulus for regurgitation;

making an initial adjustment of a distance across the first and second sides of the annuloplasty ring with the delivery system if regurgitation is detected, the initial adjustment stressing the elastic-plastic metallic core past a material yield stress so that the distance across the first and second sides is reduced by a first increment;

making second and subsequent step-wise adjustments of the distance across the first and second sides of the annuloplasty ring with the delivery system if regurgitation is again detected, the second and subsequent step-wise adjustments also stressing the elastic-plastic metallic core past the material yield stress so that the distance across the first and second sides is reduced by second and subsequent increments; and detaching the delivery system from the annuloplasty ring and removing the delivery system from the patient, and closing up any access incisions made.

In the second method, the steps of pre-installing, advancing and anchoring may be accomplished after placing the patient on cardiopulmonary bypass and by first making a series of access incisions, wherein the access incisions are sealed around the sheath of delivery system and the patient is removed from bypass prior to ensuring the heart is beating. Further, wherein the step of viewing may be accomplished using echocardiography.

Each method disclosed herein also encompass one or more simulations of the method, which are useful, for example, for teaching, demonstration, testing, device development, and procedure development. For example, methods for treating or diagnosing a patient include corresponding simulated methods performed on a simulated patient. Suitable simulated patients or anthropogenic ghosts can include any combination of physical and virtual elements. Examples of physical elements include whole human or animal cadavers, or any portion thereof, including, organ systems, individual organs, or tissue; and manufactured cadaver, organ system, organ, or tissue simulations. Examples of virtual elements include visual simulations, which can be displayed on a screen; projected on a screen, surface, space, or volume; and holographic images. The simulation can also include one or more of another type of sensory input, for example, auditory, tactile, and olfactory stimuli.

A further understanding of the nature and advantages will become apparent by reference to the remaining portions of the specification and drawings.

BRIEF DESCRIPTION OF THE DRAWINGS

Features and advantages will become appreciated as the same become better understood with reference to the specification, claims, and appended drawings wherein:

6

Figure 1:
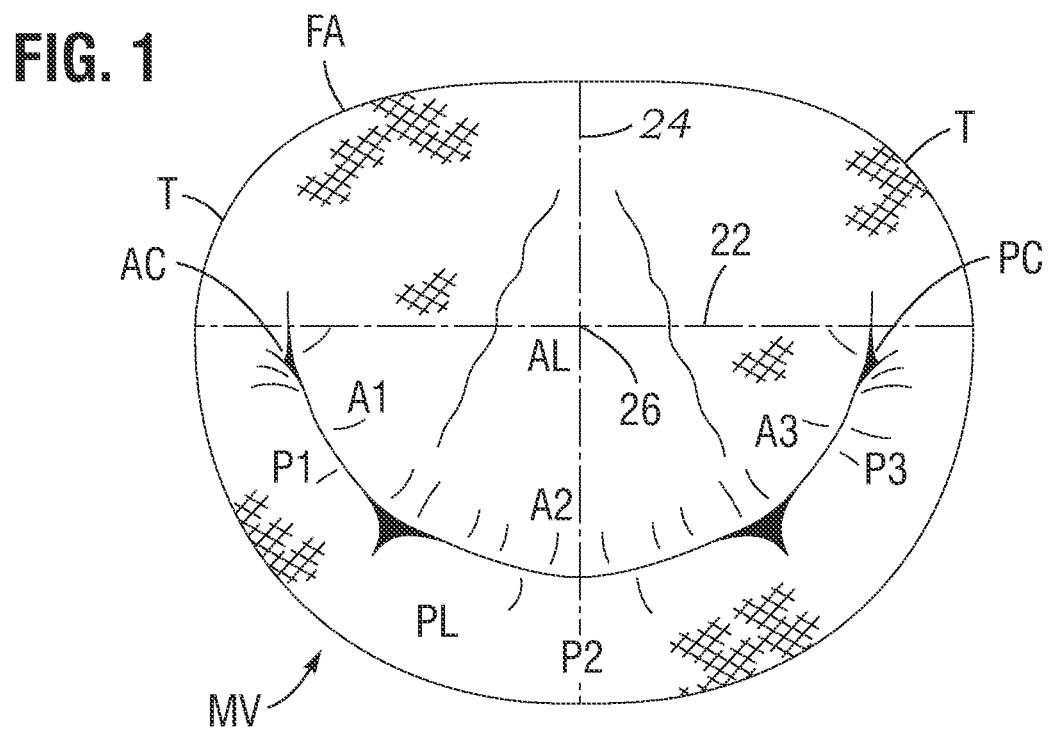
FIG. 1 is a superior or plan view of a healthy mitral valve, with the leaflets closed and coapting at peak contraction pressures during ventricular systole and indicating the primary anatomical landmarks.
Figure 2:
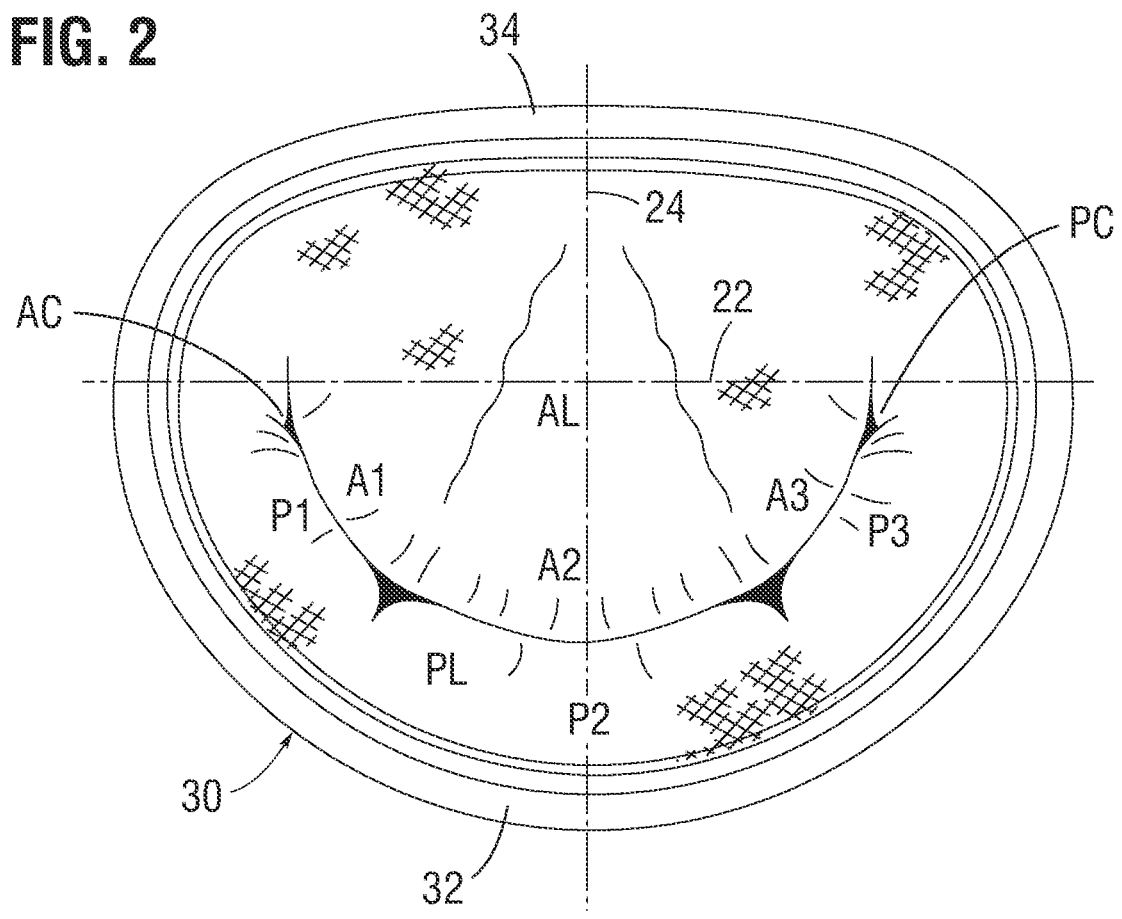
Figures 4A, 4B:
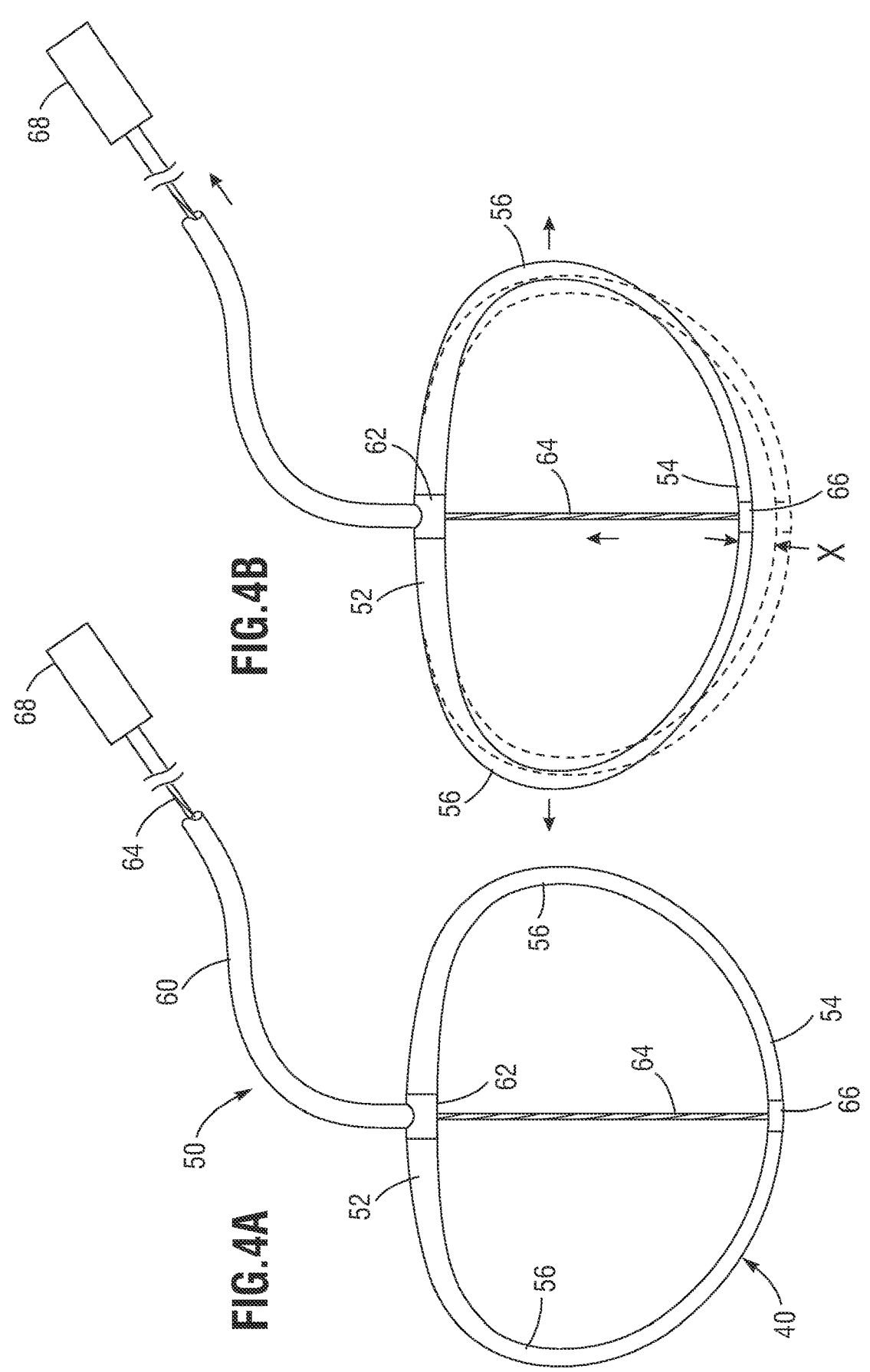
Figures 5A, 5B:
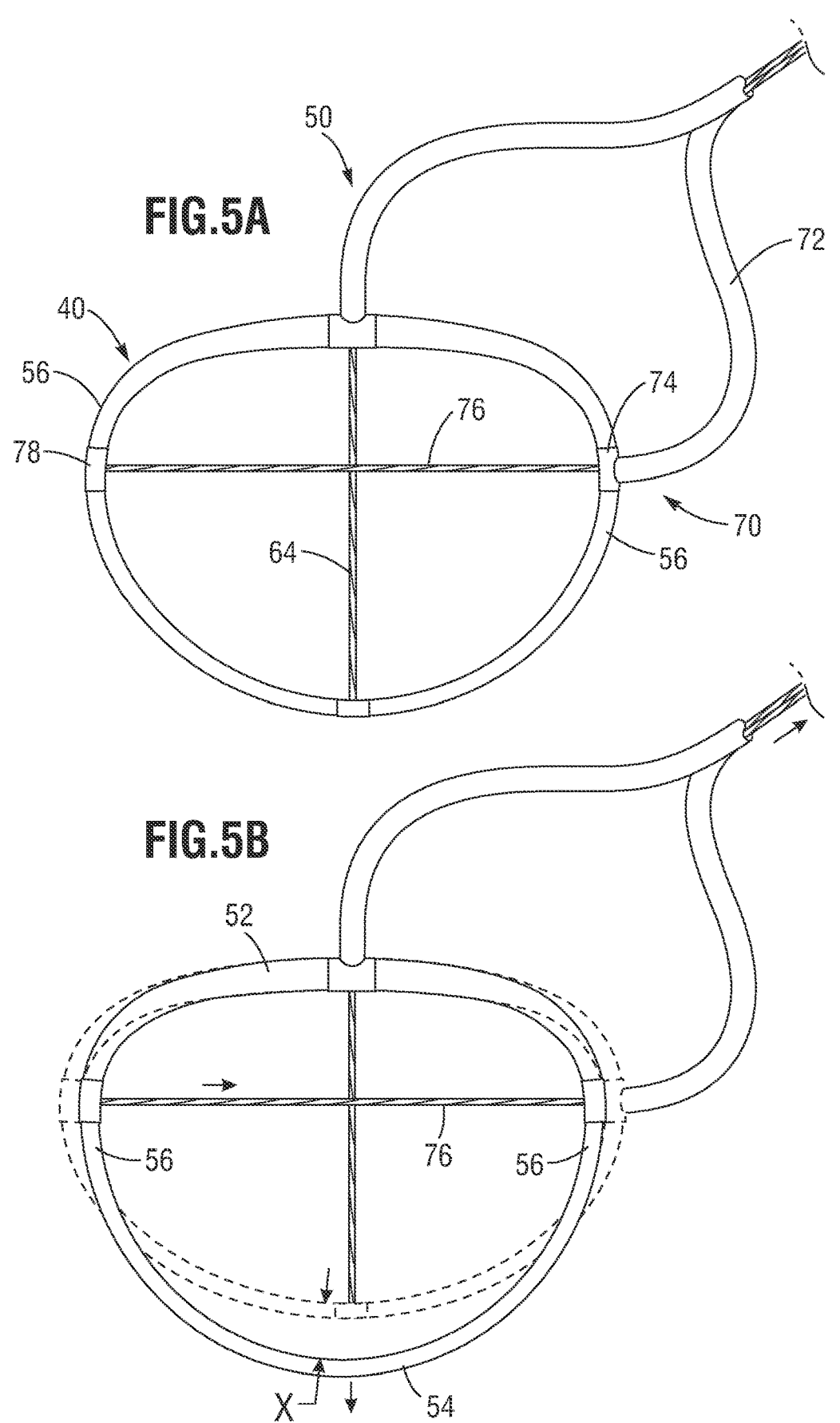
Figures 6A, 6B, 7A, 7B, 8A, 8B:
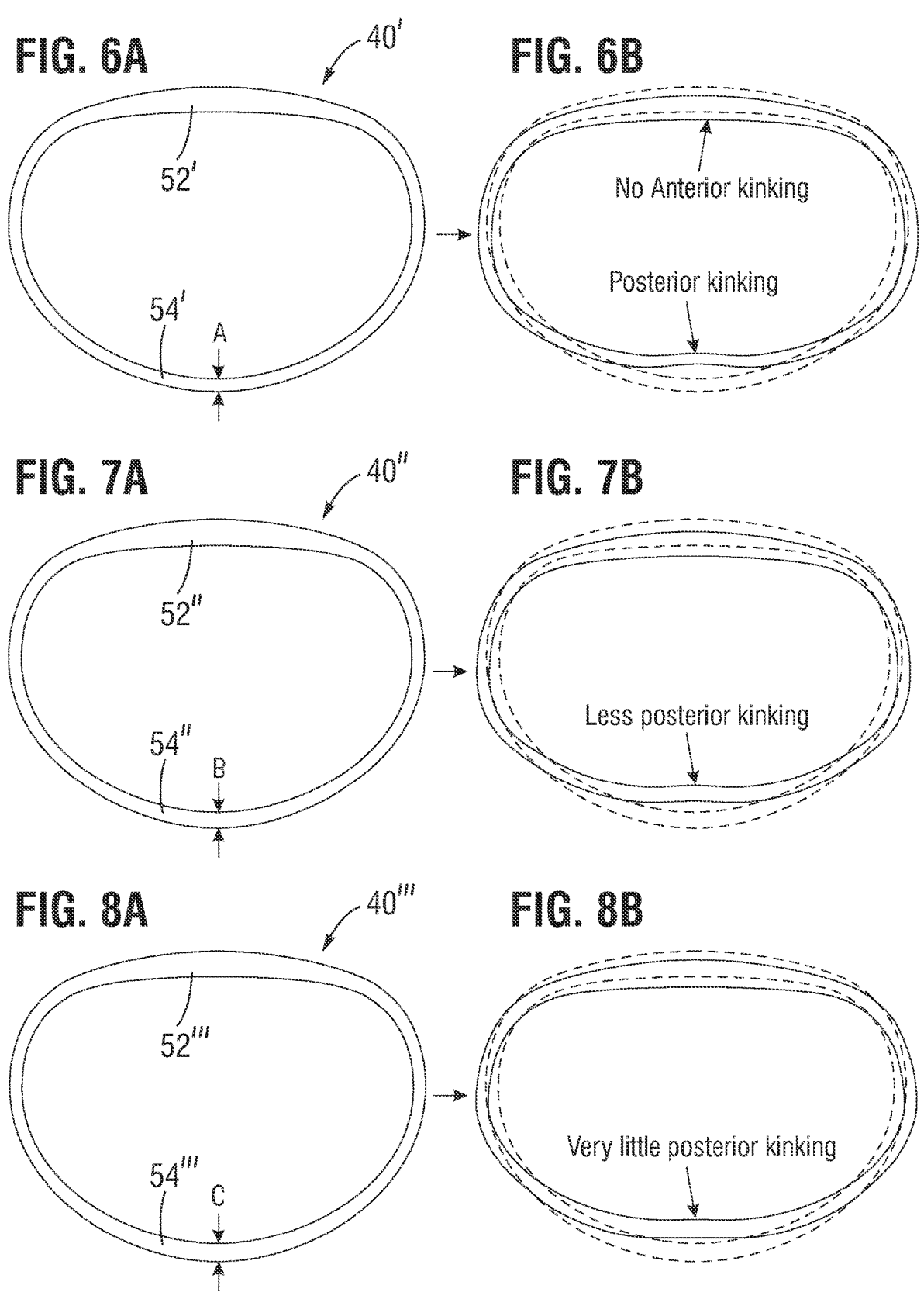
Figures 9A, 9B:
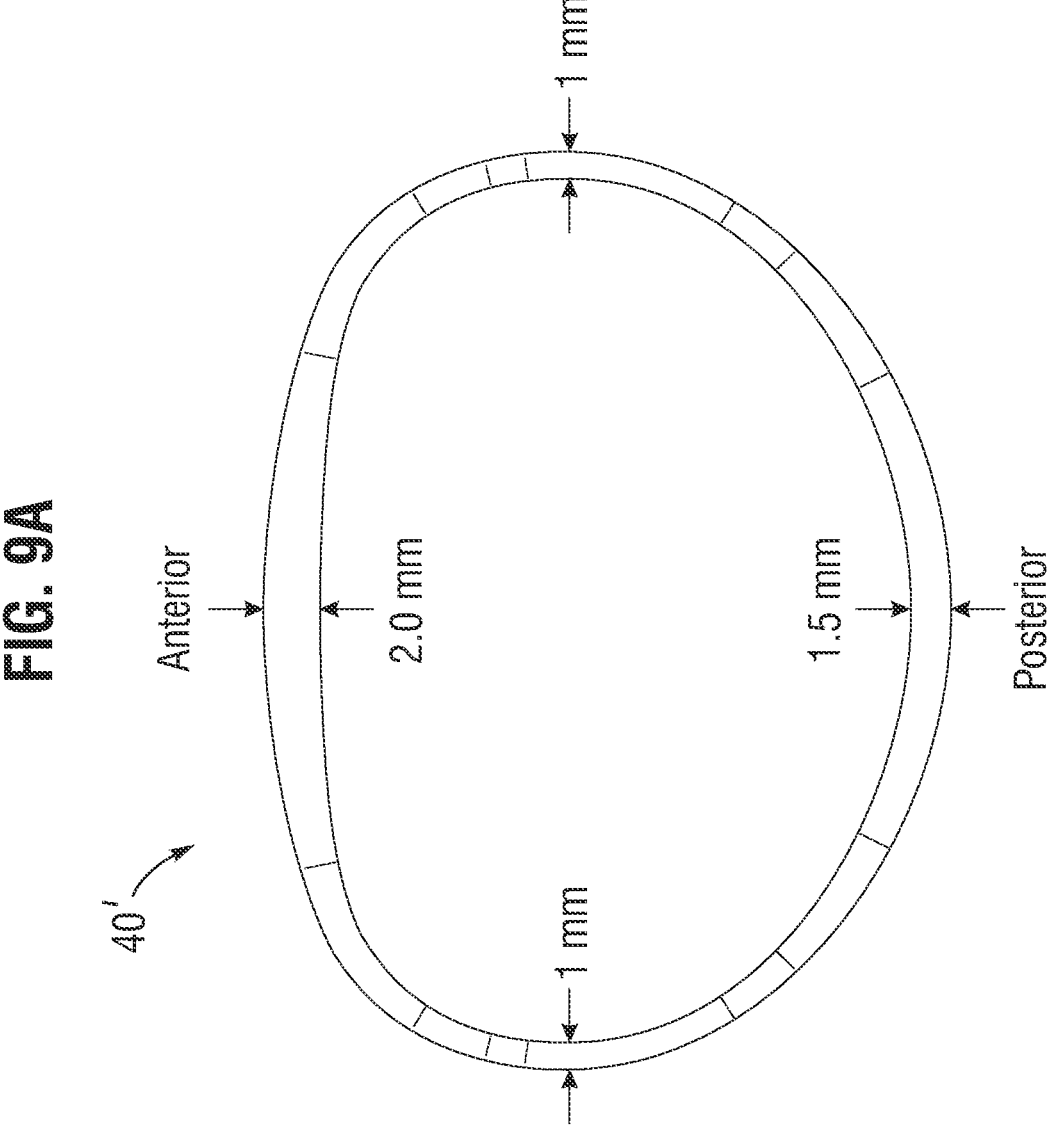
Figure 10A:
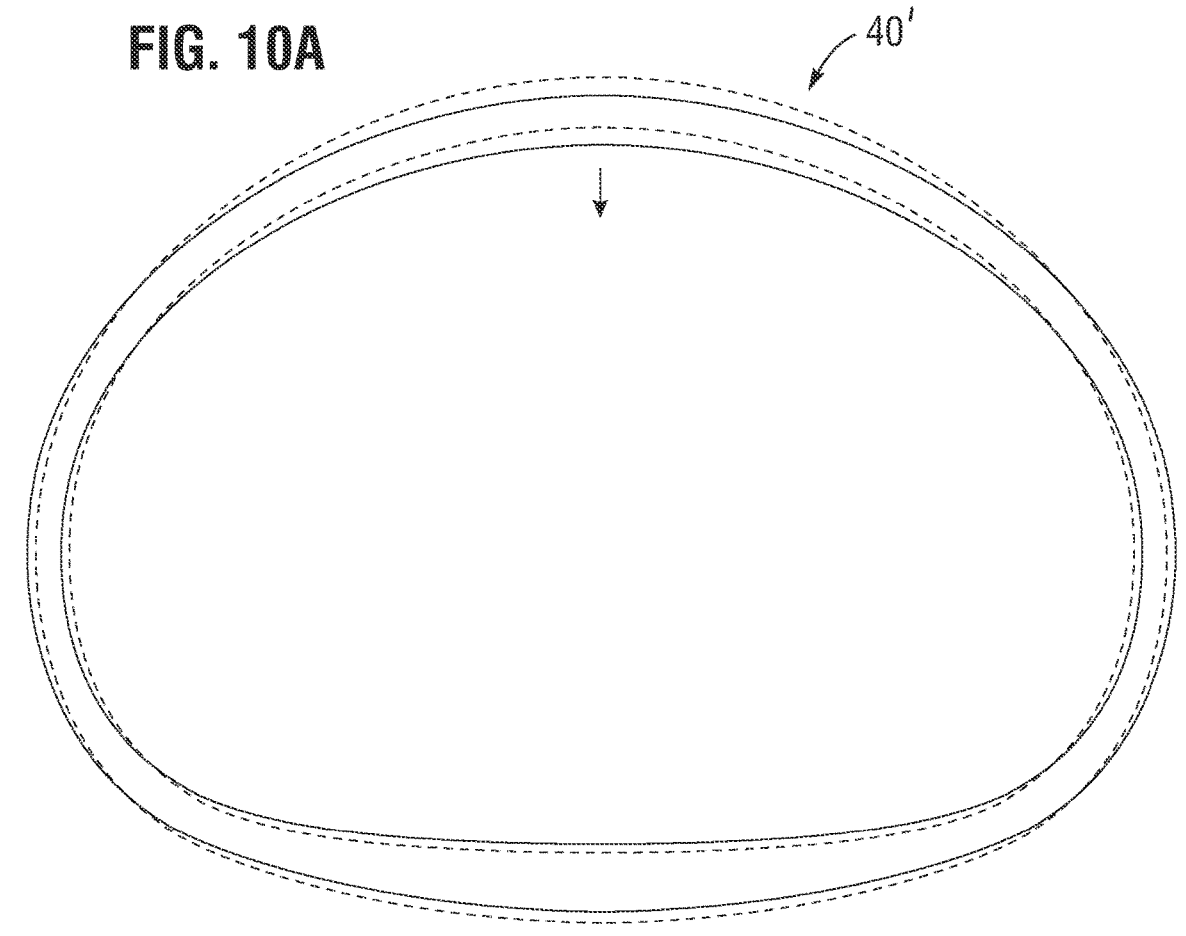
Figure 10B:
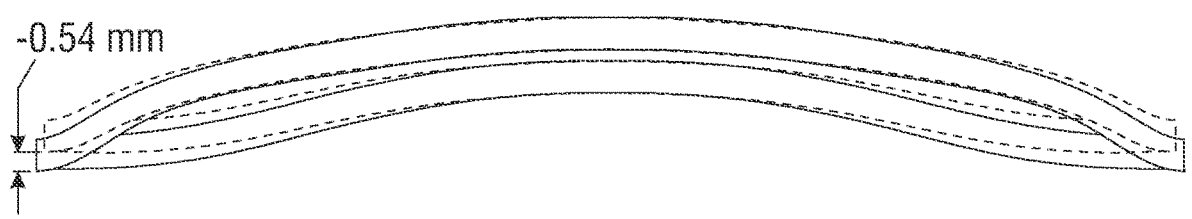
Figure 12A:
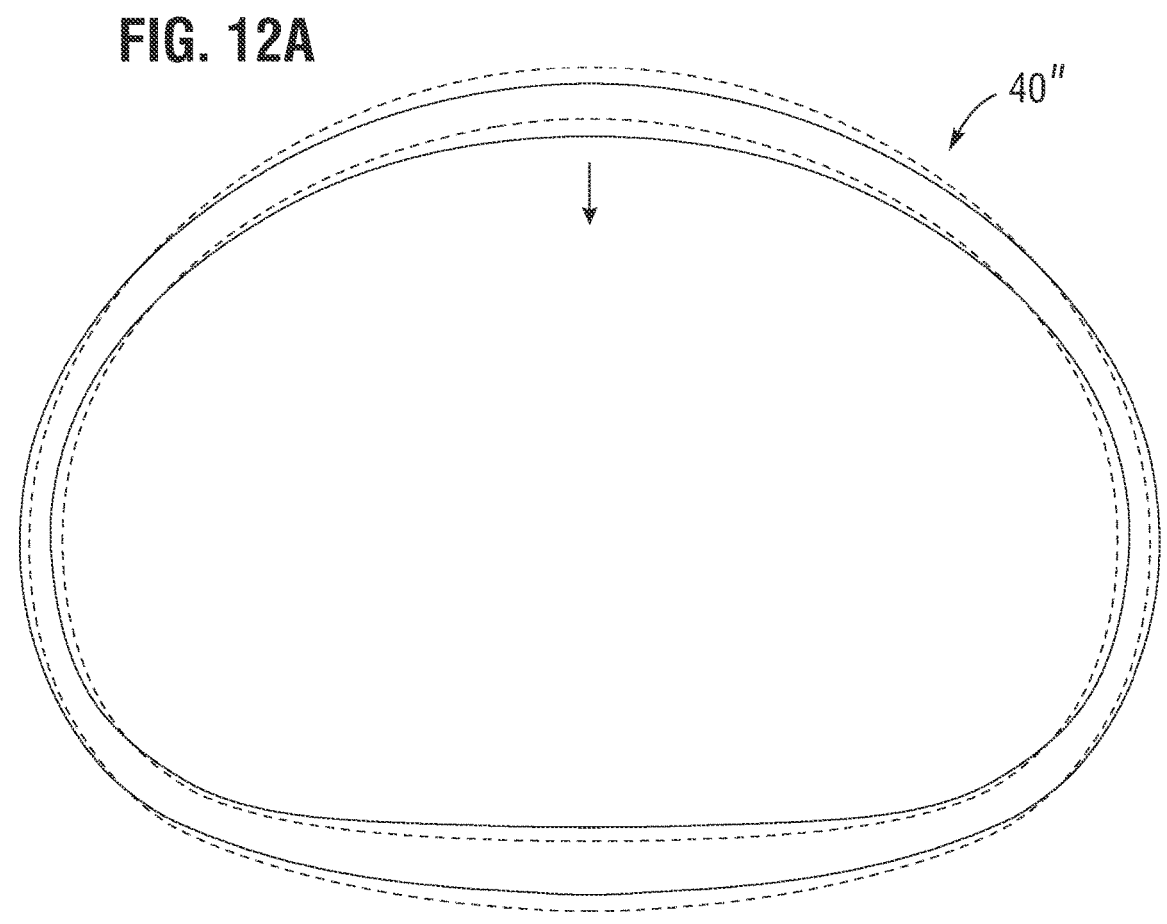
Figure 12B:
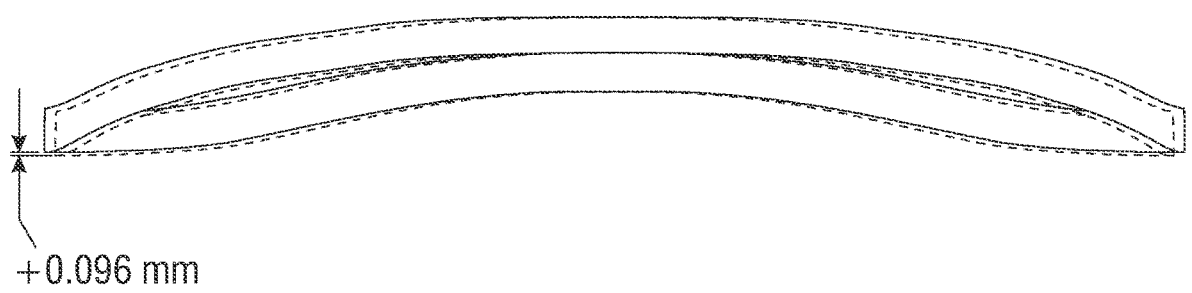
Figure 13:
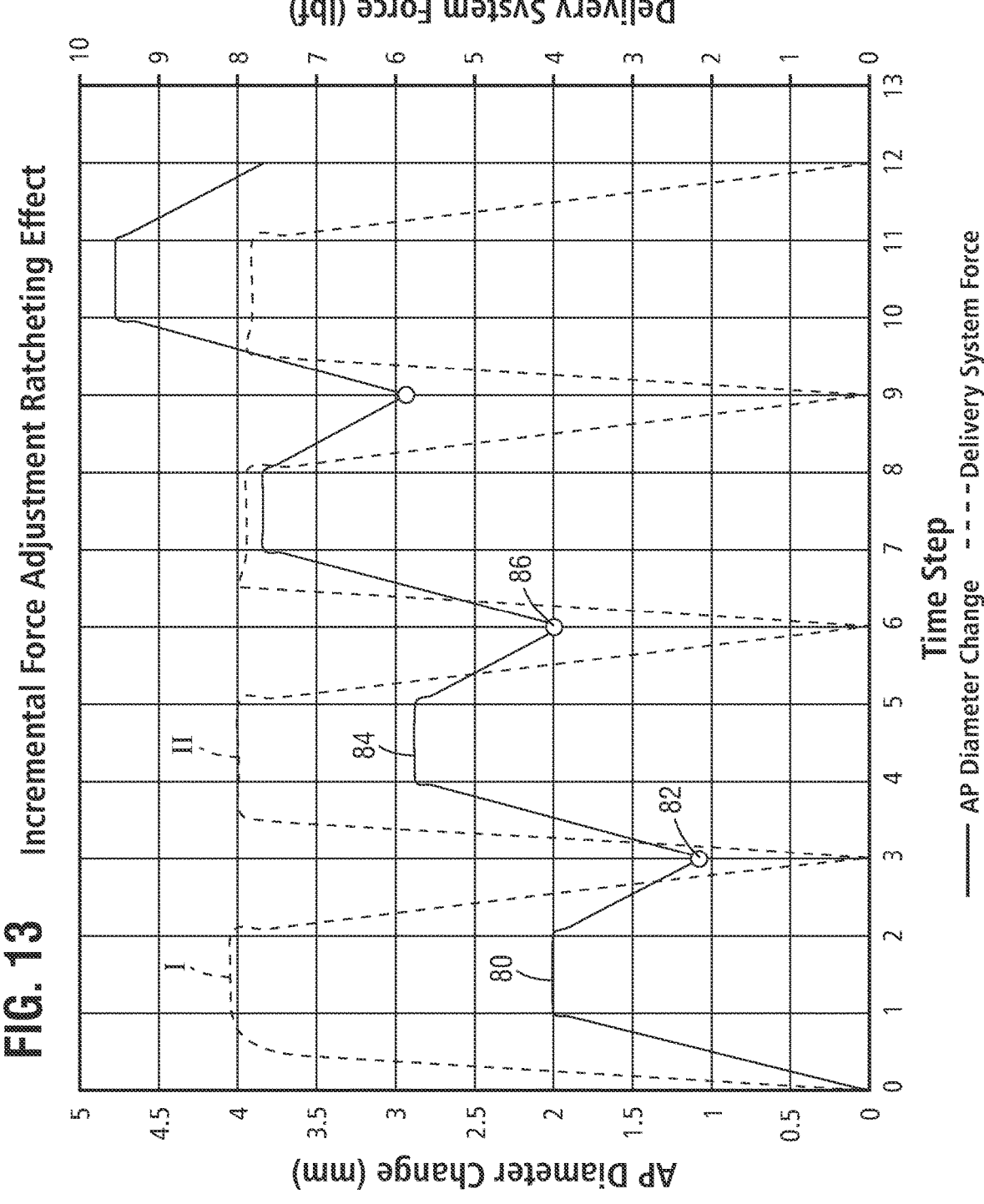
Figure 14:
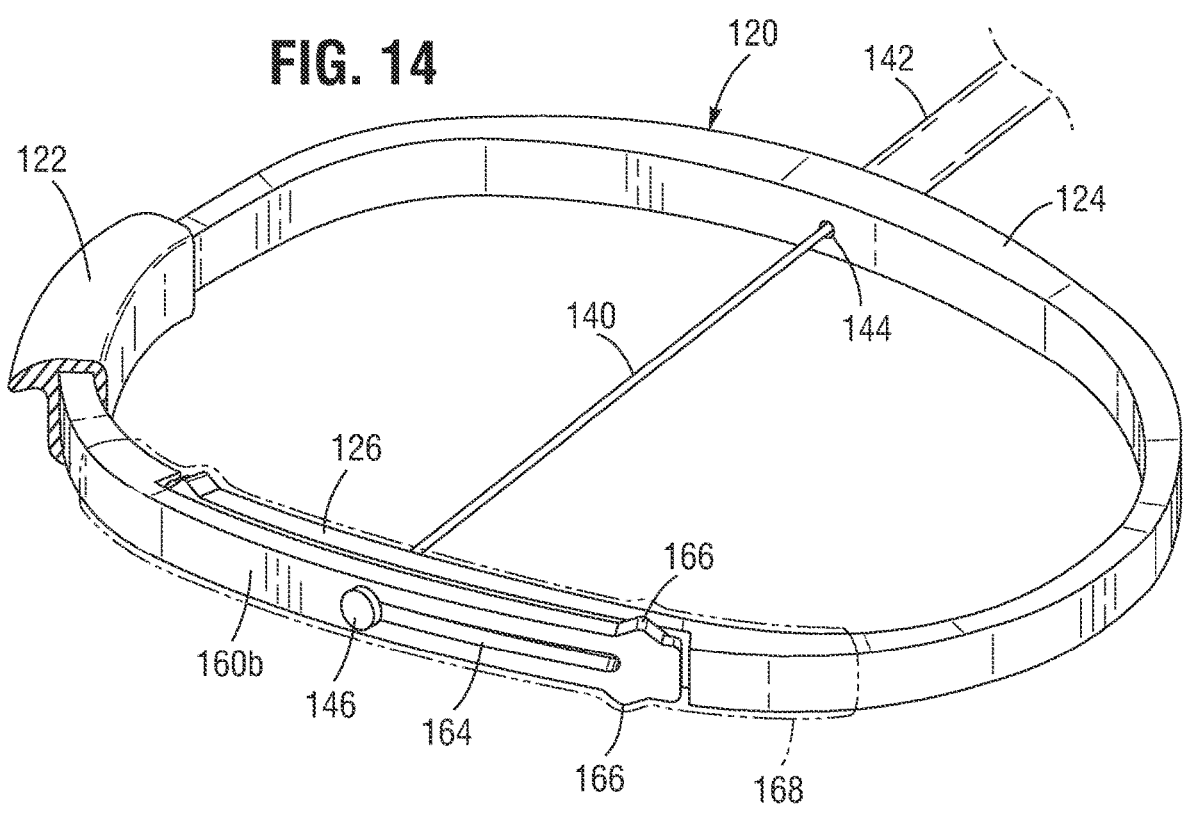
Figure 15:
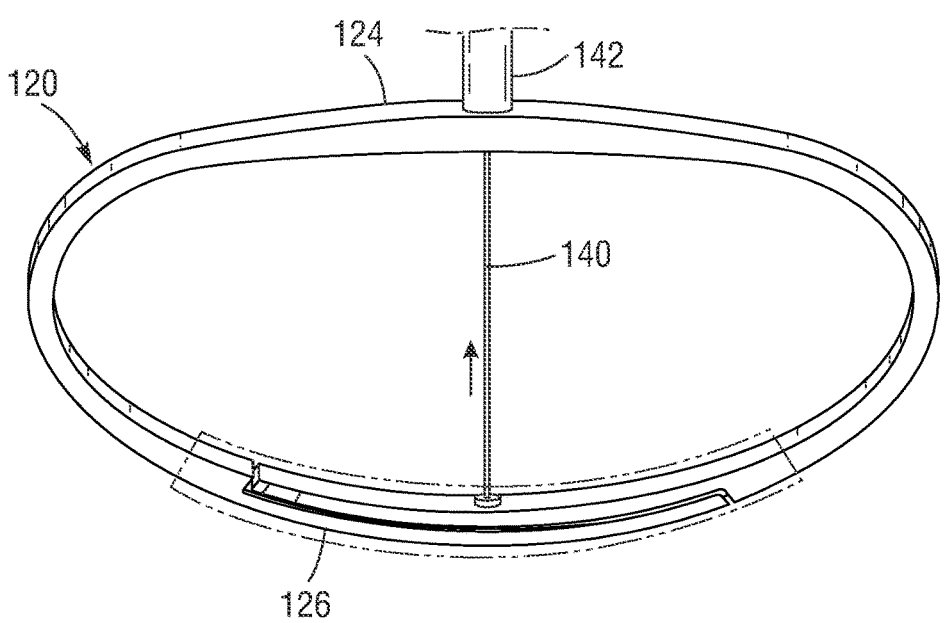
Figures 16, 17:
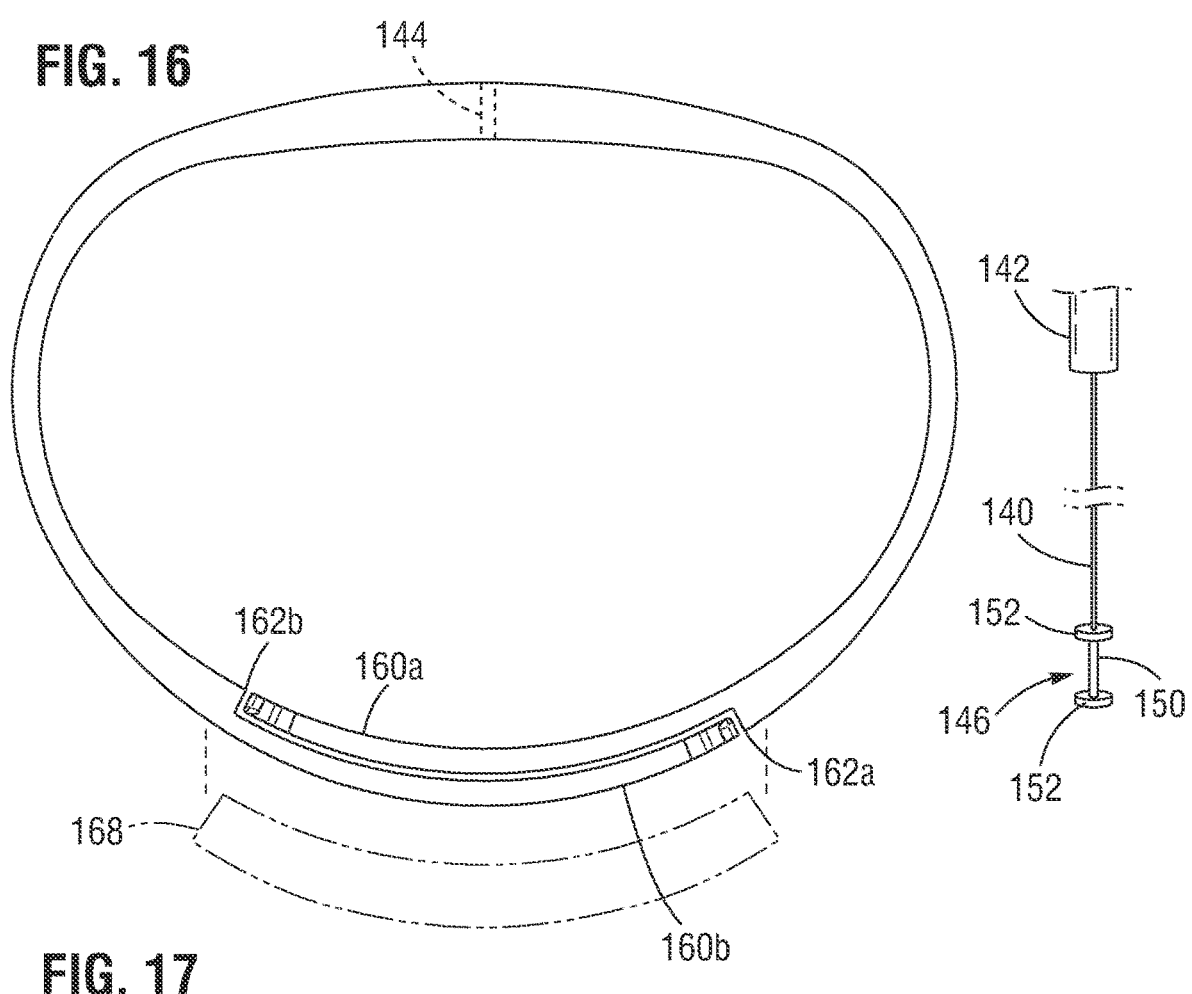
Figures 18A, 18B, 18C:
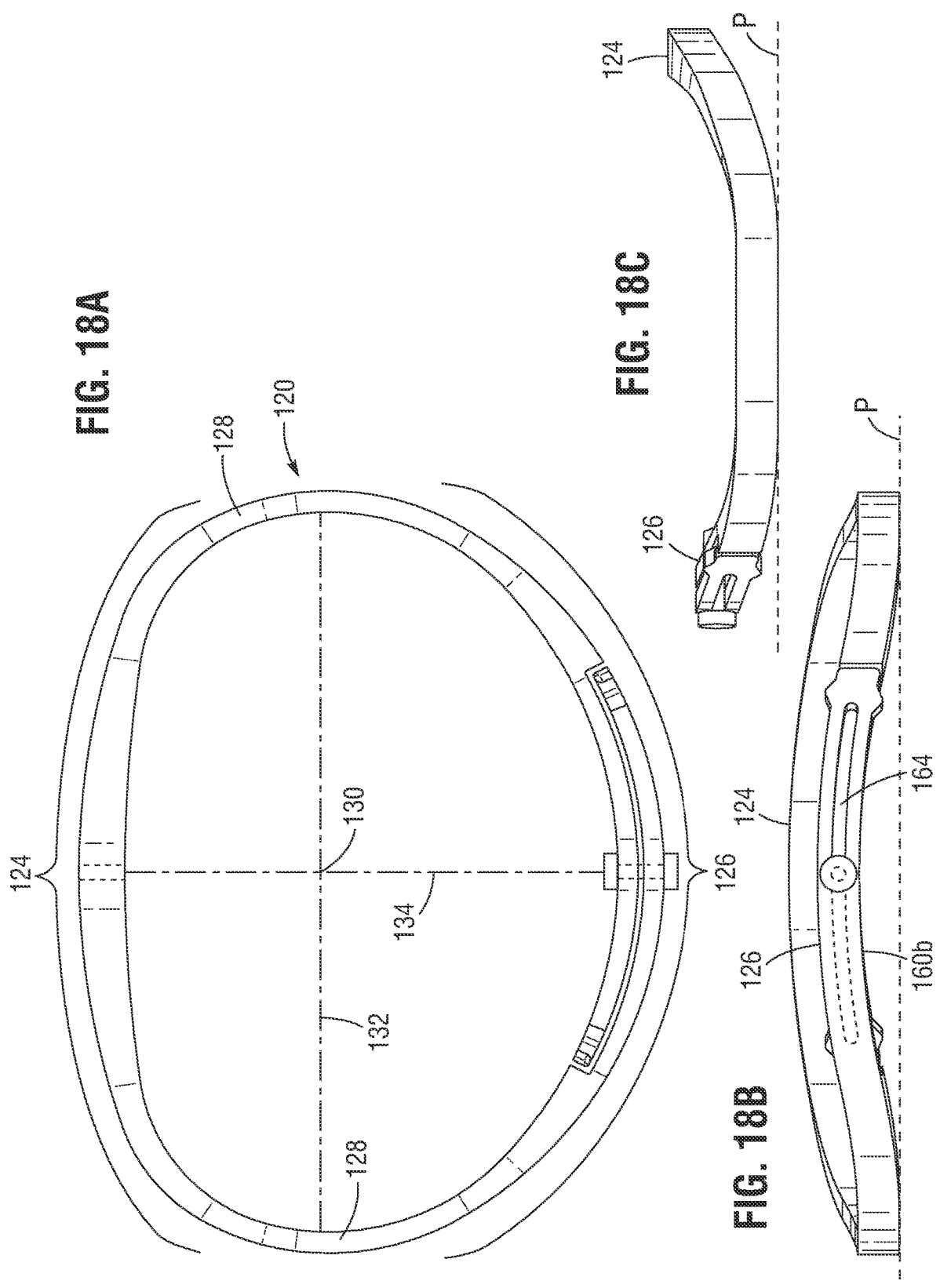
Figures 19, 20:
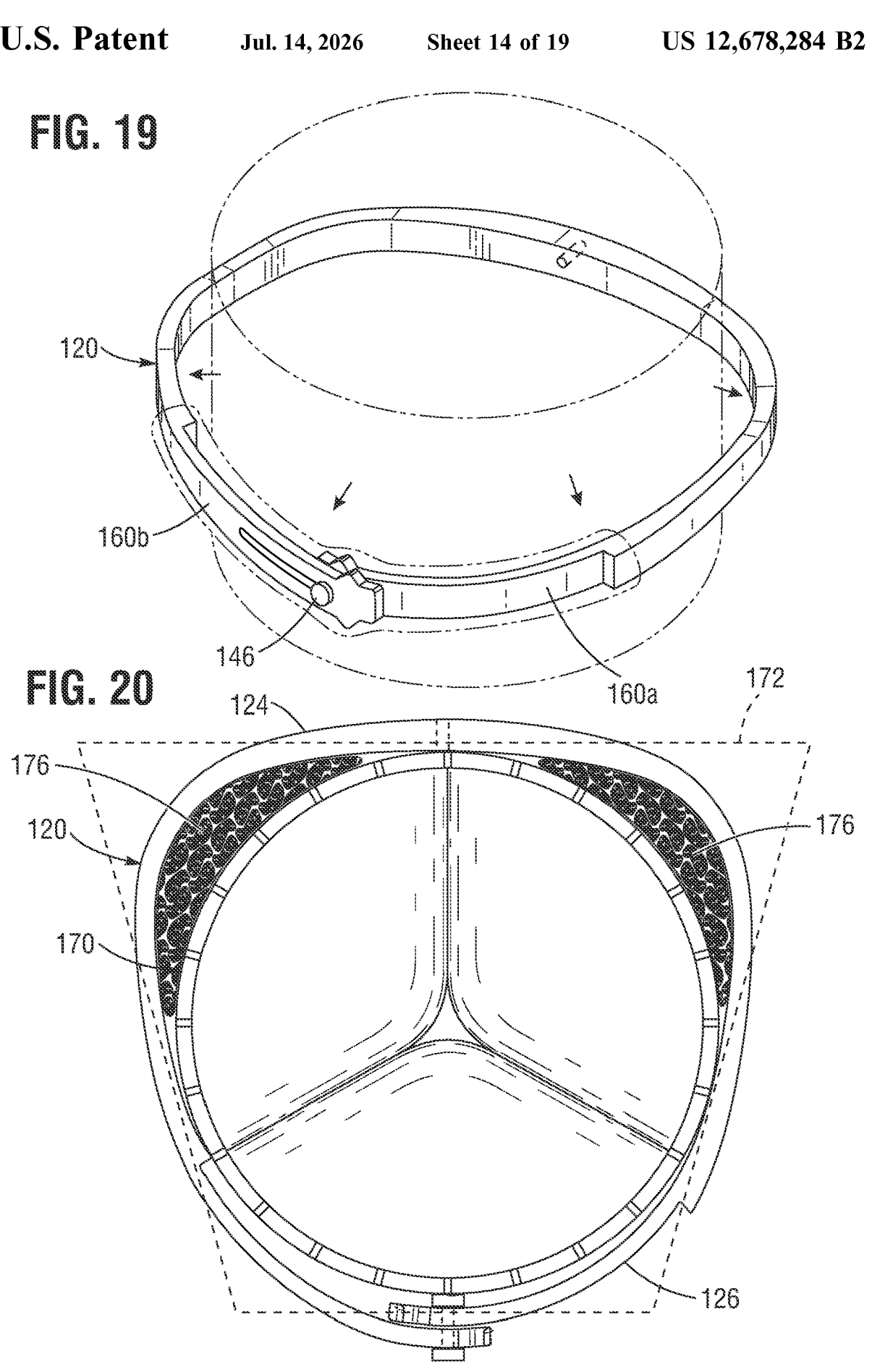
Figure 21:
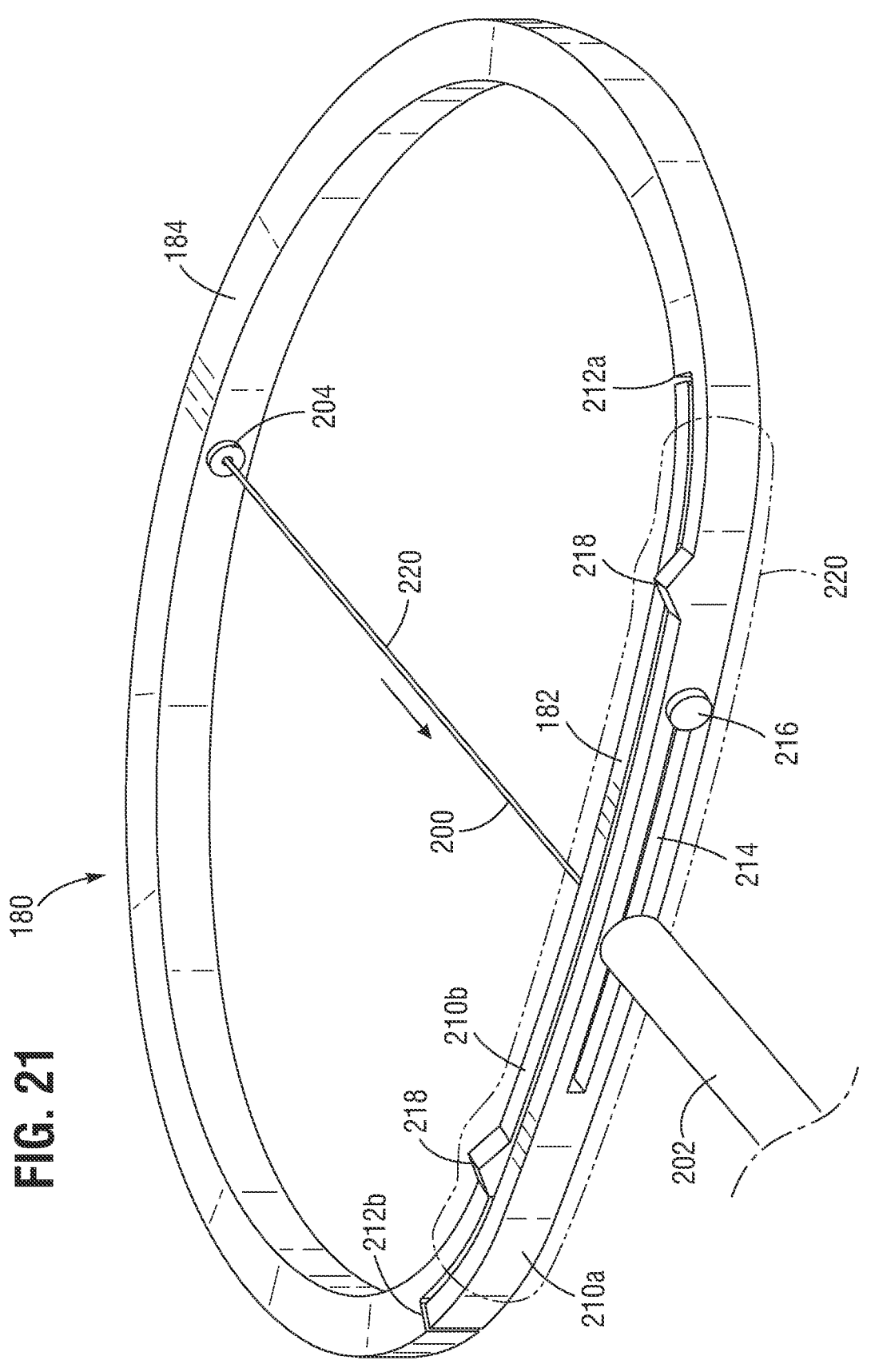
Figures 22A, 22B, 22C:
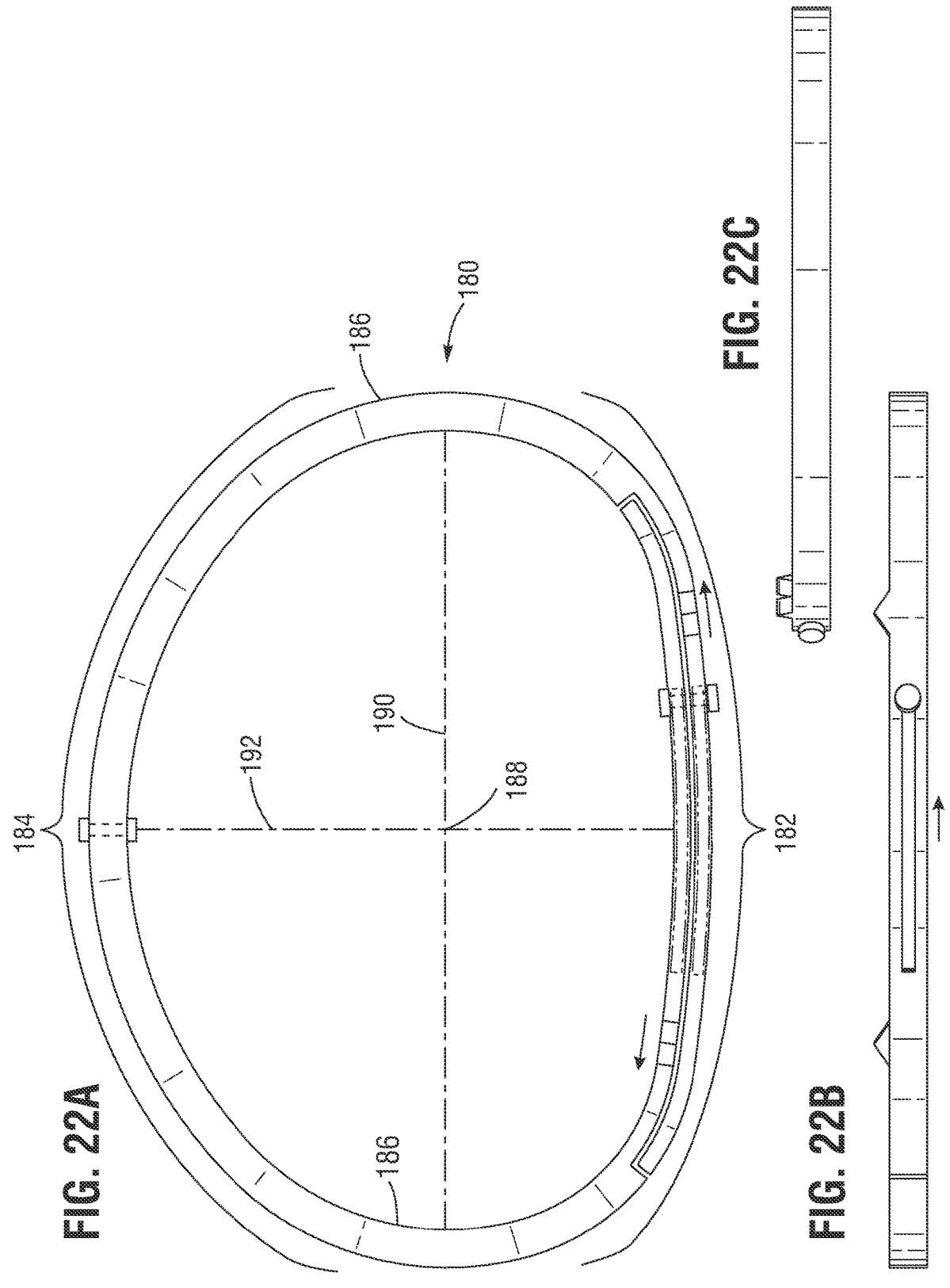
Figures 23A, 23B:
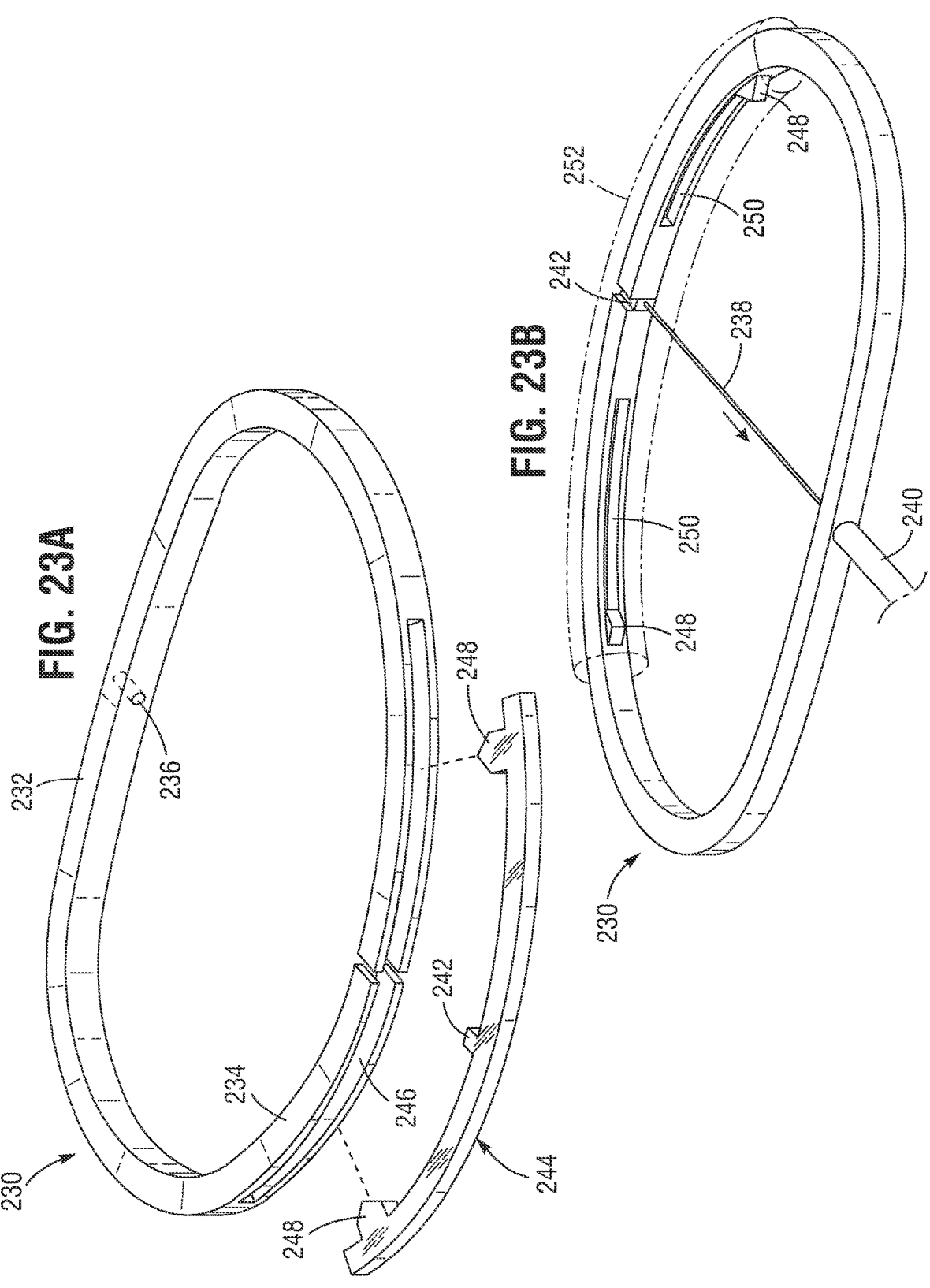
Figures 24A, 24B, 24C:
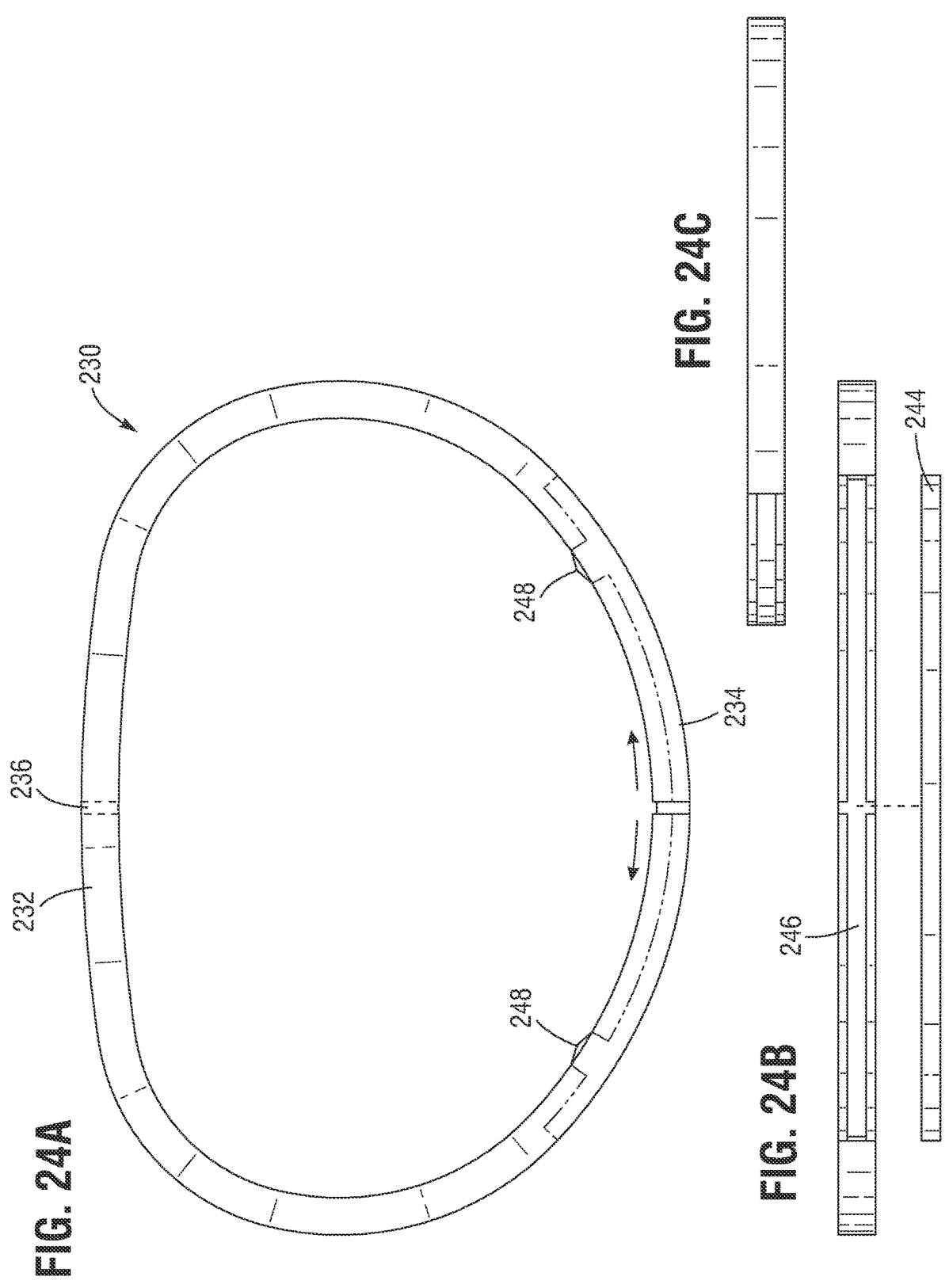
Figures 25, 26:
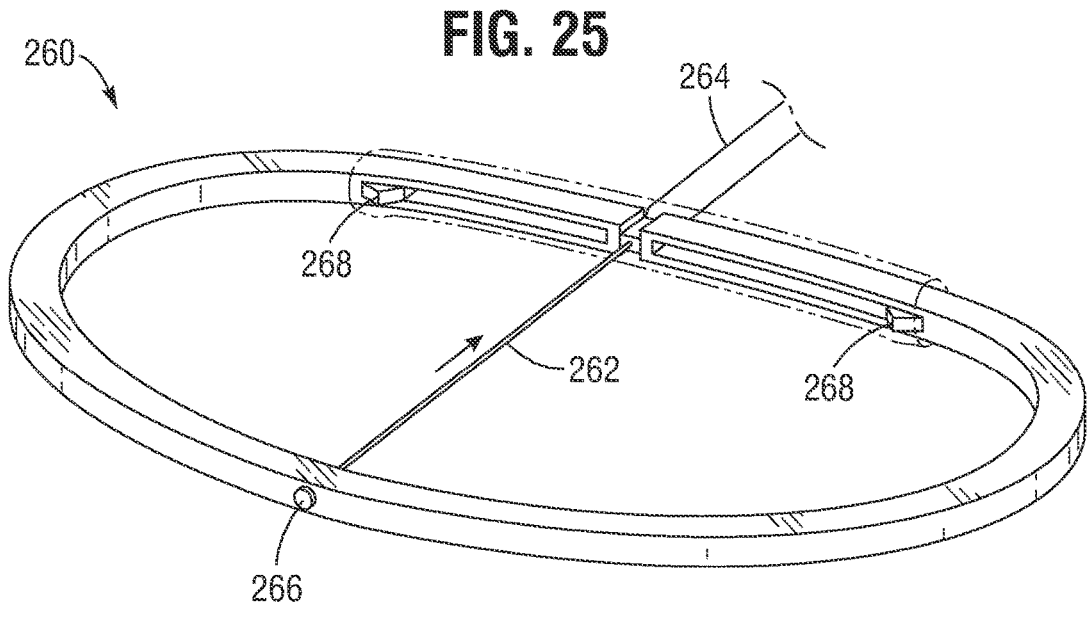

FIG. 2 is a plan view of a mitral valve as in FIG. 1 with an exemplary annuloplasty ring of the present application shown implanted therearound;

FIGS. 3A-3D are orthogonal and sectional views of the exemplary annuloplasty ring of the present application;

FIG. 4A is a plan view of the exemplary annuloplasty ring core having a shape adjustment mechanism incorporated therein that extends across the minor axis, and FIG. 4B is a plan view showing deformation of the ring core by the shape adjustment mechanism;

FIG. 5A is a plan view of the exemplary annuloplasty ring core having two shape adjustment mechanisms incorporated therein that extend across both the major and minor axes, and FIG. 5B is a plan view showing deformation of the ring core by the shape adjustment mechanism along the major axis;

FIG. 6A is a plan view of an inner core of an annuloplasty ring having a first set of radial thicknesses, and FIG. 6B is a schematic plan view of the inner core after deformation along a minor axis;

FIG. 7A is a plan view of an inner core of an annuloplasty ring having a second set of radial thicknesses, and FIG. 7B is a schematic plan view of the inner core after deformation along a minor axis;

FIG. 8A is a plan view of an inner core of an annuloplasty ring having a third set of radial thicknesses, and FIG. 8B is a schematic plan view of the inner core after deformation along a minor axis;

FIG. 9A is a plan view of an inner core of an annuloplasty ring showing particular radial thicknesses, and FIG. 9B is a side elevational view of the inner core showing particular axial thicknesses;

FIG. 10A is a plan view of the inner core in FIG. 9A after deformation along a minor axis, and FIG. 10B is a front elevational view of the inner core showing attendant axial deformation;

FIG. 11A is a plan view of an inner core of an annuloplasty ring showing particular radial thicknesses, and FIG. 11B is a side elevational view of the inner core showing particular axial thicknesses;

FIG. 11C is an enlarged portion of the middle of an anterior segment of the inner core of FIG. 11A;

FIG. 12A is a plan view of the inner core in FIG. 11A after deformation along a minor axis, and FIG. 12B is a front elevational view of the inner core showing attendant axial deformation;

FIG. 13 is a graph showing incremental application of a delivery system force to an annuloplasty ring as well as corresponding actual dimensional change of the annuloplasty ring due to material spring back;

FIG. 14 is a perspective view of an alternative annuloplasty ring inner core of the present application having a shape adjustment mechanism incorporated therein in addition to post-implant expansion capability;

FIG. 15 is a plan view of the inner core of FIG. 14 showing adjustment of the shape of the core post-implant;

FIG. 16 is an exploded plan view of the inner core of FIG. 14 and the shape adjustment mechanism;

FIG. 17 is a plan view of the inner core of FIG. 14 before and after post-implant expansion;

FIGS. 18A-18C are orthogonal views of the inner core of FIG. 14 illustrating preferred three-dimensional contours;

FIG. 19 is a schematic perspective view showing the inner core of FIG. 14 being expanded post-implant;

FIG. 20 is a plan view of the inner core of FIG. 14 after expansion with an expandable prosthetic heart valve positioned therein;

FIG. 21 is a perspective view of another annuloplasty ring inner core having a shape adjustment mechanism and post-implant expansion capability;

FIGS. 22A-22C are orthogonal views of the inner core of FIG. 21;

FIG. 23A is a perspective exploded view of a still further annuloplasty ring inner core with post-implant expansion capability, and FIG. 23B is a perspective view of the inner core with a shape adjustment mechanism incorporated therein;

FIGS. 24A-24C are orthogonal views of the inner core of FIG. 23A;

FIG. 25 is a perspective view of another annuloplasty ring inner core having a shape adjustment mechanism and post-implant expansion capability; and FIG. 26 is a plan view of still another annuloplasty ring inner core adapted for post-implant shape adjustment and expansion.

DETAILED DESCRIPTION OF CERTAIN EXAMPLES

The preferred plan view shape of the disclosed annuloplasty ring 30 is kidney or rounded D-shaped so as to conform to the peripheral shape of the usual mitral annulus.

The right ventricle RV and left ventricle LV are separated from the right atrium RA and left atrium LA, respectively, by the tricuspid valve TV and mitral valve MV; e.g., the atrioventricular valves. Though correction of the mitral annulus is the primary focus of the present application, it should be understood that certain characteristics of the annuloplasty rings described herein may equally be used to treat the tricuspid valve TV, and thus the claims should not be constrained to the mitral ring unless expressly limited.

The term "axis" in reference to the illustrated annuloplasty rings, and other non-circular or non-planar rings, refers to a line generally through the centroid of the ring periphery when viewed in plan view. "Axial" or the direction of the "axis" can also be viewed as being parallel to the average direction of blood flow within the valve orifice and thus within the ring when implanted therein. Stated another way, an implanted mitral ring orients about a central flow axis aligned along an average direction of blood flow through the mitral annulus from the left atrium to the left ventricle.

FIG. 1 is a plan view of the mitral valve with posterior being down and anterior being up. In a healthy heart, the annulus of the mitral valve MV creates an anatomic shape and tension such that a posterior leaflet PL and an anterior leaflet AL coapt in the flow orifice, forming a tight junction, at peak contraction or systolic pressures, as seen in FIG. 1. The mitral valve MV annulus has a posterior aspect to which the posterior leaflet PL attaches and an anterior aspect to which the anterior leaflet AL attaches. Where the leaflets meet at the opposing medial and lateral sides of the annulus are called the leaflet commissures: the anterior (or more accurately, the anterio-medial) commissure AC, and the posterior (or postero-lateral) commissure PC.

The posterior leaflet is divided into three scallops or cusps, sometimes identified as P1, P2, and P3, starting from the anterior commissure and continuing in a counterclockwise direction to the posterior commissure. The posterior scallops P1, P2, and P3 circumscribe particular arcs around the periphery of the posterior aspect of the annulus, which may vary depending on a variety of factors, including actual measurement of the mitral valve posterior leaflet scallops, and surgeon preference. As a rule, however, a major axis 22 of the mitral annulus intersects both the first and third posterior scallops P1 and P3, approximately at the commissures AC, PC, and a minor axis 24 intersects and generally bisects the middle posterior scallop P2. The anterior leaflet also features scallops or regions labeled A1, A2, and A3 as indicated in FIG. 1. A central flow axis 26 is arbitrarily defined at the intersection of the major and minor axes 22, 24.

As illustrated, the mitral annulus has a kidney or rounded D-shape around its periphery. The mitral anterior leaflet AL attaches to a somewhat straight fibrous portion FA of the mitral annulus, which makes up about one-third of the total mitral annulus circumference. The anterior fibrous annulus FA, the two ends of which are called the fibrous trigones T, forms part of the central fibrous skeleton of the heart. The arcuate muscular portion of the mitral annulus constitutes the remainder of the mitral annulus, and the posterior leaflet PL attaches thereto. The anterior commissure AC and the posterior commissure PC are located just posterior to each fibrous trigone.

The fibrous mitral valve annulus FA is intimate with or adjacent to the aortic valve AV, in particular the left coronary sinus LCS and non-coronary sinus NCS. The central fibrous body is fairly resistant to elongation, and thus the great majority of mitral annulus dilation occurs in the arcuate posterior two-thirds of the annulus, or around the muscular mitral annulus.

FIG. 2 illustrates the mitral valve and anatomical landmarks with an exemplary annuloplasty ring 30 secured thereto. Mitral rings are typically symmetric relative to the minor axis 24 of the annulus, but the ring 30 may also be asymmetric in this regard. Looking down on the mitral valve as in FIG. 2, the vertical minor axis 24 extends through the midpoint of both leaflets AL, PL.

Figures 3A, 3B, 3C, 3D:
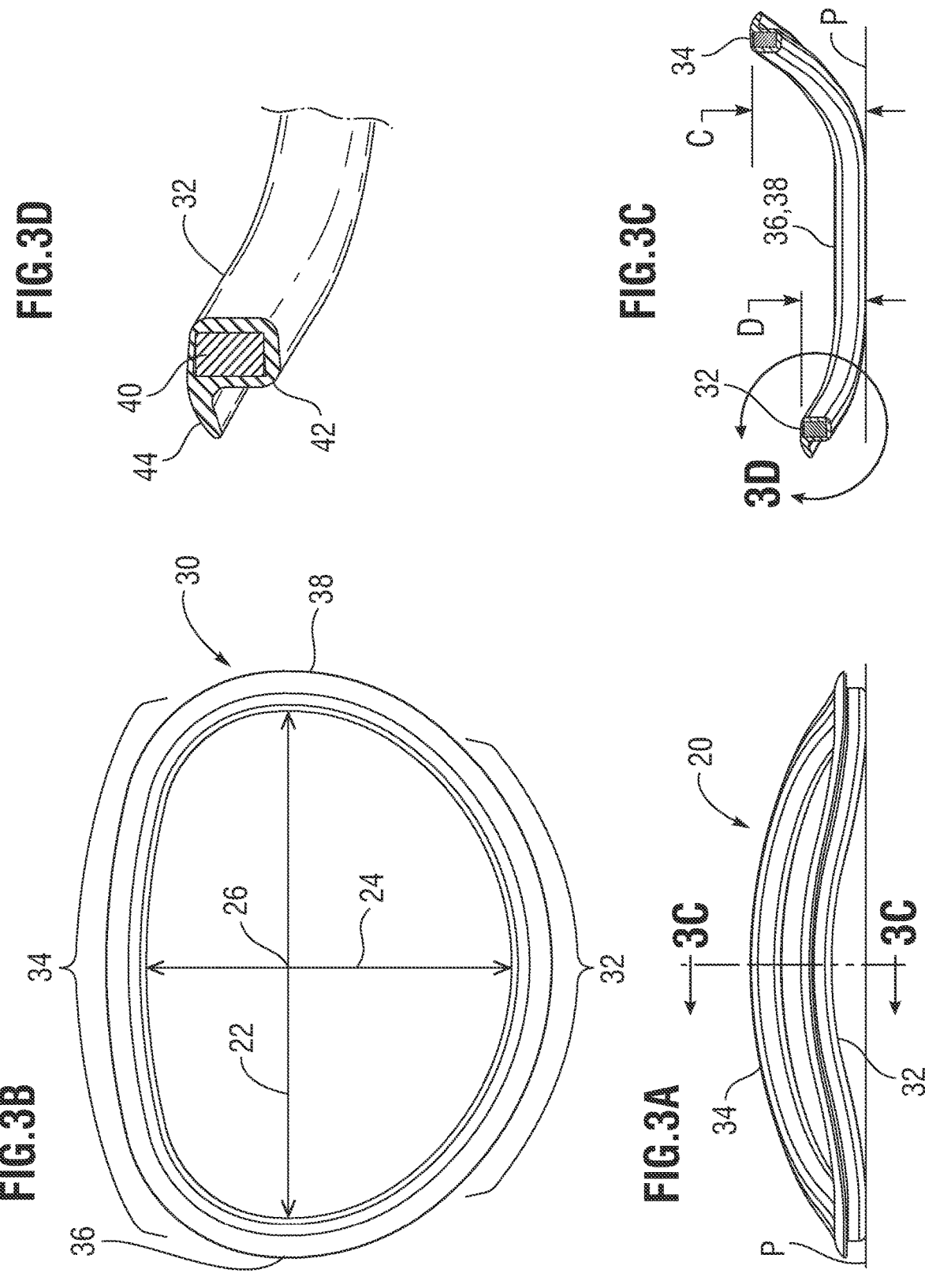

As seen in FIGS. 3A-3C, the exemplary annuloplasty ring 30 has a posterior segment 32 opposite an anterior segment 34, with side segments 36, 38 in between. Some nomenclature has the posterior segment 32 extending roughly around the posterior leaflet PL (FIG. 2), extending between the leaflet commissures AC, PC, but generally the posterior segment 32 is bisected by the minor axis 24 and extends at least around the middle posterior scallop P2 of the posterior leaflet PL. The plan view shape of the annuloplasty ring 30 is kidney or rounded D-shaped so as to conform to the peripheral shape of the typical mitral annulus.

The annuloplasty ring 30 may be three-dimensional with an upward bow in the posterior segment 32 as well as an upward bow in the anterior segment 34, as seen in FIGS. 3A and 3C. Preferably the anterior segment 34 bows upward a distance C from a reference plane P more than an upward bow D of the anterior segment 34. The side segments 36, 38 may lie in the reference plane P such that the ring 30 is partially planar with the two opposite upward bows, to form somewhat of a saddle shape. The shape of the ring 30 is similar to that of the Physio II® annuloplasty ring available from Edwards Lifesciences of Irvine, CA.

FIGS. 3C and 3D are sectional views of the annuloplasty ring 30 taken along corresponding section line 3C-3C in FIG. 3A. In a preferred example, the ring construction includes a relatively rigid inner core 40 surrounded by a suture-permeable interface. In the illustrated example, the inner core 40 is solid and rectangular, with a greater axial dimension than radial dimension. As will be explained below, the material of the inner core 40 is an elastic-plastic metal such as Stainless Steel or Titanium alloy which permanently deforms after reaching a yield stress.

The interface may include an elastomeric sleeve 42 closely surrounding the core and a fabric outer cover (not shown), for example, a polyethylene terephthalate (PET) fabric cover. In the preferred example the elastomeric sleeve 42, which may be silicone rubber, is molded to have a radially outwardly-extending flange 44 to facilitate suturing of the ring 30 to the mitral annulus. The ring 30 may be secured with sutures, staples, or other such devices to an inside ledge of the mitral annulus. In a typical procedure, an array of sutures is anchored through the annulus and then threaded through corresponding locations around the interface on the outside of the ring 30, and then the ring is parachuted down the suture array to be seated at the annulus before tying off the sutures.

With reference now to FIG. 4A, a plan view of an exemplary annuloplasty ring core 40 is shown having a shape adjustment mechanism 50 incorporated therein that extends across the minor axis of the ring core. As with the overall annuloplasty ring 30, the ring core 40 defines an anterior segment 52 opposite a more curved posterior segment 54, with lateral side segments 56 therebetween. The ring core 40 forms the primary structural component of the annuloplasty ring 30, and thus defines the kidney or rounded D-shape of the ring as mentioned. The shape adjustment mechanism 50 has an elongated flexible sheath 60 that is coupled to a proximal cable housing boss 62 affixed in the center of the anterior segment 52. An elongated flexible cable 64 extends through the hollow sheath 60 and through the cable housing boss 62, and is freely slidable through both. The cable 64 extends across the ring core 40 and is coupled to a distal cable housing boss 66 affixed in the center of the posterior segment 54. The cable 64 may be a braided metal such as stainless steel or nitinol, Ultra-high-molecule-weight polyethylene (UHMWPE) such as DYNEEMA® UHMWPE, synthetic fiber such as KEVLAR® aramid, or some other fiber-based cord, or various forms of polymer suture.

The shape adjustment mechanism 50 also may comprise a delivery system for the annuloplasty ring 30. That is, the ring 30 may be advanced and delivered to the target annulus on the distal end of the elongated sheath 60. As mentioned above, the annuloplasty ring 30 may be delivered surgically or through minimally-invasive techniques, such as through reduced size access ports. The delivery system desirably includes a handle actuator 68 from which the flexible cable sheath 60 and cable 64 extend. The handle actuator 68 includes a conventional mechanism for pulling the cable 64 relative to the sheath 60, such as a rotatable dial/spool or linear slider.

FIG. 4B is a plan view showing deformation of the ring core 40 by the shape adjustment mechanism 50. Tension on the flexible cable 64 pulls the cable through the outer sheath 60 and through the proximal cable housing boss 62. As the cable 64 is anchored to the distal cable housing boss 66, the posterior segment 54 of the ring core 40 is pulled toward the anterior segment 52, as shown. The dimension X indicates the reduction in distance across the minor axis of the ring core 40 from pulling on the cable 64. The anterior segment 52 of the ring core 40 is desirably thicker than the posterior segment 54 which causes most of the reduction in anterior-posterior (A-P) dimension of the ring core to be due to deformation of the posterior segment.

At the same time, the lateral side segments 56 are expanded somewhat due to the continuous nature and elasticity of the ring core 40, though testing and optimization of the cross-section of the ring core around its periphery can minimize the lateral expansion.

Now referring to FIG. 5A, a plan view of the exemplary annuloplasty ring core 40 shows two shape adjustment mechanisms 50, 70 incorporated therein that extend across both the major and minor axes. As before, a primary shape adjustment mechanism 50 includes a tensioning cable 64 extending across the minor axis of the ring core 40. A secondary shape adjustment mechanism 70 includes an elongated flexible sheath 72 coupled to a first lateral cable housing boss 74 located at a midpoint of one of the lateral sides 56. An elongated flexible cable 76 passes through a lumen in the sheath 72 and through the first lateral cable housing boss 74, and extends across a major axis of the ring core 40 to be affixed to a second lateral cable housing boss 78 located at a midpoint of the other of the lateral sides 56. The cable 64 may be a braided metal such as stainless steel or Nitinol, Ultra-high-molecular-weight polyethylene (UHMWPE) such as DYNEEMA® UHMWPE (Royal DSM, Heerlen, the Netherlands), synthetic fiber such as KEVLAR® aramid (DuPont, Wilmington, Delaware), or some other fiber-based cord, or various forms of polymer suture.

FIG. 5B is a plan view showing deformation of the ring core 40 by the secondary shape adjustment mechanism 70 along the major axis. Tension on the flexible cable 76 pulls the cable through the outer sheath 72 and through the first lateral cable housing boss 74. Since the cable 76 is anchored to the second lateral cable housing boss 78, the two side segments 56 are pulled toward each other. Due to the elasticity and continuous structure of the ring core 40, the posterior segment 54 experiences outward expansion away from the anterior segment 52. It is believed that only the primary shape adjustment mechanism 50 that narrows the distance between the anterior segment 52 posterior segment 54 is required. However, to provide additional resolution in the shaping of the ring core 40, both the primary and secondary shape adjustment mechanisms 50, 70 may be incorporated.

Although not shown, each of the elongated flexible cables 64, 76 may be remotely detached from the respective cable housing bosses to which they are anchored. For example, each of the cables 64, 76 may be secured to its cable housing boss by a constant minimal tension, whereas introducing slack to the cable enables detachment. Alternatively, each of the cables 64, 76 may be constructed (such as a braided metal cable) so as to be able to transmit torque along its length such that detachment of the cable from the cable housing boss may be accomplished by twisting the cable about its axis and unscrewing a threaded tip from the boss. Alternatively, the cables 64, 76 may be sutures that route through the respective bosses 66, 78 and then loop back to the delivery system handle. In this way, at the end of the procedure, the surgeon would simply need to disconnect one end of the suture from the handle and then pull it to "floss" it out as the delivery system is pulled out. Releasing one end of the cable at the delivery system handle and flossing it out greatly simplifies things. Those of skill in the art will understand there are a number of configurations that may be utilized. Likewise, coupling of the cable sheaths 60, 72 to their respective cable housing bosses 62, 74 may be remotely disconnected in similar ways, such as using threaded connections. Consequently, the shape adjustment mechanisms 50, 70 may be remotely detached and removed once the annuloplasty ring 30 has been modified in vivo.

As mentioned, the annuloplasty ring 30 may be implanted using surgical or minimally-invasive techniques. In a surgical technique, the patient's heart is stopped and patient put on cardiopulmonary bypass. The surgeon accesses the mitral or tricuspid annulus and installs anchoring sutures around the annulus. The sutures are brought outside the body and passed through the outer suture-permeable interface of the ring 30, such as shown above in FIG. 3D. The ring 30 is then advanced along the array of anchoring sutures into contact with the target annulus, and the sutures tied off. During this process, the primary the shape adjustment mechanism 50 (and secondary shape adjustment mechanism 70 if included) remains integrated with the ring 30.

Subsequently, the access incisions are sealed around the sheath 60 and the patient is removed from bypass so that the normal functioning of the heart can be restarted. At this point, echocardiography or other visualization technique can be used to determine the effect of the ring installation on regurgitation. If any regurgitation is detected, the clinician can make an initial shape adjustment of the annuloplasty ring 30 and determine if the regurgitation is reduced. As will be explained below, the shape of the annuloplasty ring 30 can be adjusted incrementally in steps until an optimum level of regurgitation reduction is attained. Subsequently, the shape adjustment mechanism 50 is decoupled from the ring 30 and removed from the body. In a preferred example, the sheath 60 of the shape adjustment mechanism 50 extends through access incisions from outside the body and through one of the walls of the heart, and the access incisions are fitted with purse-string sutures so that they can easily and rapidly be closed upon removal of the sheath.

FIG. 6A is a plan view of an inner core 40' of an annuloplasty ring having a first set of radial thicknesses. FIG. 6B is a schematic plan view of the inner core 40' after deformation along a minor axis, such as by using the shape adjustment mechanism 50. In this example, an anterior segment 52' is substantially thicker than a posterior segment 54' having a radial dimension A, such that deformation along the minor axis creates significant posterior kinking with no anterior kinking. The posterior kinking is undesirable, and thus the radial thickness of the posterior segment 54' should be increased.

FIG. 7A is a plan view of a second inner core 40'' of an annuloplasty ring having a second set of radial thicknesses, and FIG. 7B is a schematic plan view of the inner core after deformation along a minor axis. In this case, the radial thickness of the posterior segment 54'' has been increased to dimension B, which results in less posterior kinking as before. However, little or no posterior kinking is desired.

Finally, FIG. 8A is a plan view of a third inner core 40''' of an annuloplasty ring having a third set of radial thicknesses; specifically, the posterior segment 54''' has a radial dimension C. FIG. 8B is a schematic plan view of the inner core after deformation along a minor axis, showing very little posterior kinking. Testing and verification of various thicknesses of ring cores thus produces desirable results.

In addition to deformation in the radial plane as seen in plan view, the three-dimensional annuloplasty ring cores 40 also tend to permanently deform in axial planes as seen and elevational views. For example, FIG. 9A is a plan view of an inner core 40' of an annuloplasty ring showing particular radial thicknesses. Namely, the ring core 40' has a radial thickness of 2.0 mm on its anterior segment, 1.5 mm on its posterior segment, and 1 mm at both lateral side segments. FIG. 9B is a side elevational view of the inner core showing particular axial thicknesses; namely, the axial thickness is a uniform 1 mm throughout.

FIG. 10A is a plan view of the inner core 40' in FIG. 9A after permanent deformation along a minor axis, which pulls in the posterior segment as described above. FIG. 10B is a front elevational view of the inner core 40' showing attendant axial deformation. Namely, reduction of the A-P dimension of the ring core 40' causes the three-dimensional saddle shape to permanently increase; in this case, with a particular application of force, by a distance of about 0.54 mm. That is, the arc of the saddle shape increases, which may not be desirable.

FIG. 11A is a plan view of an inner ring core 40'' showing particular radial thicknesses; in this case the same as the ring 40 of FIG. 9A. FIG. 11B is a side elevational view of the inner core 40'' showing different axial thicknesses. In this case, the axial thickness at the lateral side segments is increased to about 1.25 mm.

FIG. 11C is an enlarged portion of the middle of an anterior segment 52'' of the inner ring core 40'' showing a radial cut or slit 58 opening to an exterior edge. Such a slit 58 may be formed by laser cutting, for example, to permit the ring core 40'' to conform better to an expanding prosthetic heart valve therein. That is, the slit 58 would tend to spread out when the ring core 40'' expands outward, helping to round the relatively straight anterior segment 52'' around the expanding prosthetic heart valve.

Subsequently, FIG. 12A is a plan view of the inner core 40'' in FIG. 11A after permanent deformation along a minor axis. The radial deformation seen in plan view is very similar to that of the ring core 40' as seen in FIG. 10A as the radial thicknesses have not changed. However, FIG. 12B is a front elevational view of the inner core 40'' showing attendant axial deformation. Because of the increase of the axial thickness of the lateral side segments, the ring core 40'' does not permanently deform as much in the axial direction; namely, by a positive 0.096 mm. Again, by trial and error a desirable set of radial and axial dimensions that produce particular shape changes may be obtained. In this case, axially thickening the ring core 40'' at the side segments relative to the anterior and posterior segments produced lower permanent axial deformation. For instance, the ring core 40'' may be 25-35% axially thicker at the side segments than around the other segments, with the anterior and posterior segments being about equal in axial thickness.

FIG. 13 is a graph showing incremental application of a delivery system force to an annuloplasty ring as well as corresponding actual dimensional change of the annuloplasty ring due to material spring back. The left side vertical scale shows the anterior-posterior (AP) diameter change in millimeters after application of particular deformation forces by the shape adjustment mechanism 50 seen in FIGS. 4A and 4B to a particular ring core. The right side vertical scale indicates the applied force in pounds. This horizontal scale is measured in increments of time, such as seconds. The graph shows the force application in dashed line steps, and the resulting ring core deformation in solid line.

Each of the applications of force is set at about 8 pounds and is shown as a rapidly increasing slope to a plateau of approximately one time segment (e.g., one second), before a rapid decrease of force back to zero. The resulting ring core deformation follows an equally steep trajectory to a plateau, and then when the force is removed the material of the ring core springs backward. Thus, for example, during the first application of force I the ring core experiences an AP diameter change of 2 mm at plateau 80, but then the ring core springs back to point 82 so that the final deformation is only about 1 mm. After the application of a second incremental force II, the ring core experiences a similar AP diameter change that increases from 1 mm to plateau 84 at about 3 mm from the original diameter, but then again springs back to point 86 at about 2 mm after the force is removed. This step-wise deformation of the ring core continues and permits a clinician to test out a particular deformation without committing to it. There is thus a ratcheting effect that will allow the surgeon to test a particular amount of shape change before committing to it.

Due to the malleability of the ring core, once the elastic limit of the ring core was surpassed, a portion of that displacement would become permanent, thereby conferring a new shape on the ring. However, until that elastic limit is reached, the force can be removed and the ring core resorts back to its original shape. Namely, there is an initial linear elastic region of the curve below a particular displacement, such as 1 mm. If the ring core were only deformed to that displacement and then released, it would return to its initial shape. In this way, the clinician could "test" the repair with 1 mm of AP reduction to determine if, for example, regurgitation was improved compared to the initial shape with zero displacement. If the effect on the repair was desirable, the clinician could make the change permanent by temporarily applying 2 mm of displacement to the ring core at plateau 80. If there was a degradation in performance at 2 mm of displacement relative to 1 mm, the clinician could release the tension on the delivery system control and the ring core would return to its new configuration with an AP displacement of 1 mm (point 82). If, however, there was better performance (less regurgitation, for example) at 2 mm when it was tested temporarily, then the clinician could set the new shape to 2 mm of displacement by temporarily applying 3 mm of displacement at plateau 84. If the performance were better at 2 mm of displacement than 3 mm, again they could release tension on the reshaping cable and the ring core would return from 3 mm of displacement to its new set point of 2 mm at point 86. If 3 mm were better than 2 mm, they could apply 4 mm to make the new setpoint 3 mm and evaluate the effect of 4 mm. In this way, the optimal shape of the band could be approached by reversibly trying increasing levels of displacement until a degradation in performance was found, and then returning to the previous optimal setting. This procedure could be done initially while the patient was on-pump using the saline test to evaluate the repair, and then verified and adjusted further off-pump, or the entire adjustment procedure could be done on- or off-pump.

In one alternative, the ring 30 and adjustment mechanism 50 is configured to come out of sterile packaging, or maybe after an initial preparation step, to be initially implanted with 1 mm of A-P displacement (reduction), which would be fully reversible since it is elastic. Then, in the case of needing less coaptation (such as in Systolic Anterior Motion, aka SAM), the clinician could release the ring to expand by 1 mm.

As mentioned, the material of the inner core 40 is a plastically expandable (elastic-plastic) metal such as stainless steel or titanium alloy. Finite element analysis on various models of the inner core 40 have been created to simulate the effects of applications of force at different points on the core. Elastic-plastic materials simulated include annealed Ti-6Al-4V (E=113.8 GPa, 1200 MPa yield), Annealed 316-L stainless steel (E=193 GPa, 235 MPa yield), 4 grades of commercially pure (CP) titanium (CP Ti Gm: E=100.0 GPa, Yield=240 MPa; CP Ti Gr2: E=105.0 GPa, Yield=275 MPa; CP Ti Gr3: E32 103.4 GPa, Yield=450 MPa; and CP Ti Gr4: E=105.0 GPa, Yield=550 MPa), and MP35N nickel-cobalt-chromium-molybdenum alloy (E=232.8 GPa, Yield=414 MPa). Each of these materials are conventionally used for surgical implants and may prove suitable in different situations. From these models, it was found that grades G1 and Gr2 of commercially pure (CP) titanium could be deflected by about 1 mm with very little permanent shape change, while still being able to ratchet up by about 1 mm for every 2 mm of deflection. Aside from that advantage, preferred materials have a reasonably low yield strength to keep the forces down (e.g., Yield<300 MPa), as well as favorable attributes associated with implants such as good corrosion resistance, machinability, track record of implant use, etc.

Post-Implant Expansion

Up to now, each of the annuloplasty ring inner cores have been shown and described as solid, continuous rings of particular materials and shapes. Such rings are particularly well-suited for remodeling the mitral annulus and assuming a particular shape adjustment from plastic deformation of the core material. However, it should be noted that over time the benefits of an annuloplasty repair may diminish such that a further operation is necessary. Often such operation involves implanting a prosthetic heart valve within the previously-implanted annuloplasty ring, a so-called valve-in-ring procedure, or explant of the annuloplasty ring before implant of the new prosthetic heart valve. Obviously, the former operation is much less invasive and thus preferred.

However, patients with smaller anatomical features and thus smaller annuloplasty rings are often not well-suited for a valve-in-ring procedure because of space constraints—the valve must be relatively small to fit within the small ring, and thus does not have a sufficient flow orifice. Consequently, annuloplasty rings that are expandable post-implant have been developed to enable imposition of a larger prosthetic heart valve therein. The present application contemplates annuloplasty ring inner cores that have the capacity for both shape adjustment upon initial implant, and expansion down the road for a valve-in-ring procedure.

FIG. 14 is a perspective view of an alternative mitral annuloplasty ring inner core 120 having a shape adjustment mechanism incorporated therein in addition to post-implant expansion capability. The inner core 120 is desirably formed of a biocompatible elastic-plastic metal, as described above, covered with a suture-permeable interface 122 of fabric or silicone rubber and fabric, partially shown in cutaway. The annuloplasty ring thus comprises the inner core 120 surrounded by the interface 122.

As also seen in more detail in FIGS. 18A-18B, the inner core 120 defines a continuous rounded D-shape in plan view with a relatively straight anterior side 124 opposite a more rounded posterior side 126, with smaller radius lateral sides 128 in between. As with many mitral annuloplasty rings, the inner core 120 is arranged around a central flow axis 130 at the intersection of the major axis 132 and a minor axis 134. As mentioned above, the dimension across the inner core 120 along the minor axis 134 is denoted the A-P dimension, for anterior-posterior.

The annuloplasty ring 120 may be three-dimensional with an upward bow in the posterior side 126 as well as an upward bow in the anterior side 124, as seen in FIGS. 18B and 18C. Preferably the anterior side 124 bows upward a distance from a reference plane P more than an upward bow of the posterior side 126. The lateral sides 128 may lie in the reference plane P such that the ring 120 is partially planar with the two opposite upward bows, to form somewhat of a saddle shape. The shape of the ring 120 is similar to that of the Physio II® annuloplasty ring available from Edwards Lifesciences of Irvine, CA.

With reference back to FIG. 14, a shape adjustment mechanism is incorporated into the inner core 120 for the purpose of post-implant adjustment of the peripheral shape of the core. In particular, an adjustment cable 140 passes through a hollow delivery sheath 142 that abuts the anterior side 124 of the ring. The adjustment cable 140 extends through a radial bore 144 formed at a central location in the anterior side 124 and extends across the flow orifice defined within the ring to the posterior side 126. The cable 140 attaches to an anchor pin 146 a fixed within the posterior side 126 of the inner core 120. As will be explained below, the anchor pin 146 also serves as an expansion limiting pin if a subsequent post-implant expansion is necessary. Although not shown, the adjustment cable 140 attaches to the anchor pin 146 in a manner which permits easy detachment therefrom. For example, the adjustment cable 140 may be coupled to the anchor pin 146 in the manner of the flexible cables 64, 76 to the bosses 66, 78 of the ring cores 40 shown in FIGS. 4-5.

With reference to the exploded plan view of FIG. 16, the cable 140 and sheath 142 are shown separated from the ring core 120. The anchor pin 146 may comprise a spool-like element with the central shaft 150 and two end flanges 152. The shaft 150 has a length approximately equal to the radial dimension of the inner core 120 at the center of the posterior side 126, and the shaft passes radially through the posterior side such that the flanges 152 flank the core and hold the pin 146 in place.

As mentioned, the inner core 120 is formed of a biocompatible metal as described elsewhere herein susceptible to plastic deformation upon the application of shaping forces. In particular, as seen in FIG. 15 adjustment of the shape of the core 120 post-implant is depicted. Namely, tension on the adjustment cable 140 in combination with embracing the access sheath 142 against the anterior side 124 of the ring core 120 causes the posterior side 126 to be pulled toward the anterior side, reducing the A-P dimension. As explained above, this shape adjustment may be done immediately after securing the annuloplasty ring to the mitral annulus under fluoroscopy or other visualization to judge what shape best repairs the annulus. For instance, the incremental shape adjustments described above with respect to FIG. 13 may be implemented. In addition, although not shown, a second shape adjustment mechanism extending across the major axis 132 of the ring core 120 may be incorporated, such as shown in FIGS. 5A/5B. FIG. 15 illustrates reduction in the A-P dimension relative to the relaxed plan view of FIG. 18A, which may be appropriate for repairing a distended mitral annulus due to congestive heart failure, for example.

In addition, the inner core 120 is constructed to enable post-implant expansion during a valve-in-ring procedure. In particular, the inner core 120 is configured to expand at the posterior side 126 by virtue of overlapping free ends 160a, 160b. FIG. 16 shows the overlapping free ends 160a, 160b from above while FIGS. 14 and 18B illustrate detailed features.

Each of the free ends 160a, 160b has a radial thickness of approximately one half of the total radial thickness of the posterior side 126, with an axial dimension equal to the axial dimension of the posterior side. In other words, the free ends 160a, 160b are relatively thin band-like segments arranged to slide circumferentially relative to each other. Moreover, each free end 160a, 160b projects from a full radial width portion of the core so as to form radial shoulders 162a, 162b where they start. In the relaxed or contracted configuration of the inner core 120, as seen in FIG. 18A, the terminal ends of the respective free ends 160a, 160b extend into contact with the radial shoulder 162a, 162b formed by the other free end which prevents the ring circumference from reducing below that of its relaxed state. Instead, when the shape adjustment mechanism is actuated, and the posterior side

126 is pulled closer to the anterior side 124, the shape of the inner core 120 is altered rather than the core undergoing a reduction in circumference.

Each of the free ends 160a, 160b has a circumferentially-extending slot 164 that extends approximately one half its length. Therefore, as seen in FIG. 14, the outer free end 160b has a slot 164 that extends to the right of the center of the posterior side 126, while the inner free end 160a has a similar slot 164 that extends to the left. This can also be seen in the front elevational view of FIG. 18B. The shaft 150 of the anchor pin 146 is sized with approximately the same thickness as the axial dimension of the slots 164. The presence of the anchor pin 146 thus causes the free ends 160a, 160b to remain axially aligned as they slide apart. Eventually, the free ends 160a, 160b separate far enough such that the end of each of the slots 164 reaches the common anchor pin 146, thus limiting expansion of the inner core 120. This can be seen in FIG. 17 as well as in FIG. 19.

As seen in various figures, the overlapping free ends 160a, 160b each has a terminal end with axial bumps 166 that project upward and downward from adjacent sections of the inner core 120. In addition, a resilient sleeve 168 (shown in phantom) surrounds the entire length of the overlapped free ends 160a, 160b in the constricted state of the inner core 120. The resilient sleeve 168 may be formed of an elastomer such as silicone or more preferably a polyethylene terephthalate (PET) shrink tube and applies a nominal compression around the free ends 160a, 160b. This compression in conjunction with the axial bumps 166 helps prevent premature expansion of the inner core 120. That is, the friction between the bumps 166 and sleeve 168 hold the ring together until an expansion force greater than normal physiological forces is applied.

FIG. 19 is a schematic perspective view showing the inner core 120 being expanded post-implant by a balloon or an expanding prosthetic heart valve applying substantially even outward forces. FIG. 20 is a plan view of the inner core 120 after expansion with an expandable prosthetic heart valve 170 positioned therein, following a valve-in-ring procedure. It should be noted that expansion of the inner core 120 of the ring alters its peripheral shape from substantially rounded D-shape to more rounded, as seen. This is because the prosthetic heart valve 170 is substantially cylindrical when expanded and the ring conforms as much as possible around it. Any gaps susceptible to regurgitation that may be formed between the cylindrical heart valve 170 and the surrounding structure of the annuloplasty ring may be plugged in various ways, such as with the suture permeable interface 122 (see FIG. 14), outwardly projecting fabric on the valve, or sleeve-like spacers interposed between the valve and ring (not shown).

More precisely, the ring inner core 120 (and thus the ring itself) changes shape from its original rounded D-shape to something more polygonal, most closely resembling a trapezoid as indicated in the dashed line 172. The curved posterior side 126 of the ring core 120 conforms best to the expanding cylindrical heart valve 170, whereas the interstitial spaces 174 formed at the ends of the straighter anterior side 124 may require filling with fabric or other such sealing solutions. For instance, fabric plugs or seals 176, shown schematically, may be provided either on the exterior of the heart valve 170 in two locations, or may be added at the time of valve expansion.

FIG. 21 is a perspective view of another mitral annuloplasty ring inner core 180 also having a shape adjustment mechanism and post-implant expansion capability, while FIGS. 22A-22C are orthogonal views of the inner core. The inner core 180 is shown as substantially planar, though it may be three-dimensional and shaped such as the inner core 120 seen in FIGS. 14-19. Although not shown, the inner core 180 is typically surrounded by a suture-permeable interface of fabric or silicone rubber and fabric, as was described above with respect to FIG. 14.

In the plan view of FIG. 22A, the inner core 180 again defines a rounded D-shape with a relatively straight anterior side 182 opposite a more curved posterior side 184, with lateral sides 26 in between. The periphery of the core is preferably oriented about a flow axis 188 at the intersection of major axis 190 and minor axis 192.

The inner core 180 may have a variety of cross-sectional shapes, but is desirably rectangular in cross-section and formed of an elastic-plastic malleable biocompatible metal, as described above. This enables the inner core 180 to be deformed by a shape adjustment mechanism. For example, FIG. 21 illustrates a shape adjustment mechanism including an adjustment cable 200 that passes through a delivery sheath 202. The sheath 202 terminates adjacent an exterior radial face of the anterior side 182 of the inner core 180 (and preferably outside the surrounding suture-permeable interface). The adjustment cable 200 passes through the anterior side 182 and extends across the minor axis of the annuloplasty ring to be secured at an anchor pin 204 affixed at a central point within the posterior side 184 of the inner core.

As explained above, tension on the adjustment cable 200 from outside the body pulls the posterior side toward the anterior side 182, as indicated by the movement arrow, by virtue of the distal end of the delivery sheath 202 abutting the outside of the annuloplasty ring. Although it will not be described further, the capability to reduce the A-P dimension of the inner core 180, coupled with the particular material and configuration of the inner core, enables incremental adjustment of the size of the annuloplasty ring immediately after implant.

Moreover, the inner core 180 has a capability of post-implant expansion if a valve-in-ring procedure is required. As best seen in FIGS. 21 and 22A, the inner core 180 features overlapping ends 210a, 210b on the anterior side 182. The overlapping ends 210a, 210b together form the total radial thickness of the inner core 180 and are each about half the thickness and formed in relatively thin bands. The terminal ends of each of the overlapping ends 210a, 210b extends to a respective inset shoulder 212a, 212b at the start of the other band so that a continuous inner core 180 is formed which resists circumferential constriction. In this way, the peripheral shape of the inner core 180 changes from pulling on the adjustment cable 200 as opposed to a reduction in circumferential dimension.

Each of the overlapping ends 210a, 210b has a circumferential slot 214 centered on the minor axis 192 so as to be initially in alignment. A guide pin 216 having a flange on each end extends through both slots 214. The guide pin 216 both helps maintain alignment between the overlapping ends 210a, 210b and also provides a stop at a predetermined dimension of circumferential expansion. That is, the guide pin 216 is shown initially positioned at the right end of the aligned slots 214. When the two overlapping ends 210a, 210b slide apart, as indicated by the arrows in FIG. 22A, the slot 214 of the inner end 210b displaces the guide pin 260 to the left relative to the slot in the outer end 210a until the pin reaches the end of the slot in the outer end. Although not shown, it should be understood that locating the overlapping ends 210a, 210b in the middle of the relatively straight anterior side 182 changes the contour of the ultimately expanded inner core 180 from that shown in FIG. 20 where the overlapping ends are located in the center of the posterior side.

Each of the overlapping ends 210a, 210b has at least one triangular tooth 218 projecting axially upward. A resilient sleeve 220 surrounds the overlapping ends 210a, 210b. The sleeve 220 may be a polyethylene terephthalate (PET) shrink tube. Frictional engagement between the teeth 218 and the compressive sleeve 220 in addition to the presence of the surrounding suture-permeable interface (not shown) prevents the overlapping ends 210a, 210b from sliding apart under the influence of ordinary physiological forces. In this way, the inner core 180 maintains its initial constricted shape until a larger dilatory force such as from a balloon or expanding heart valve is applied.

FIG. 23A is a perspective exploded view of a still further expandable mitral annuloplasty ring inner core 230, and FIG. 23B is a perspective view of the inner core with a shape adjustment mechanism incorporated therein. The inner core 230 may be shaped substantially the same as described above with a rounded D-shaped periphery defining a straight anterior side 232 opposite a more curved posterior side 234. The inner core 230 has a radial bore 236 through the anterior side 232 through which can pass an adjustment cable 238. The adjustment cable 238 extends from a distal end of a delivery sheath 240 across the minor axis of the inner core 230 and is secured to a central boss 242 on an expansion insert 244. As seen in FIG. 23B, the adjustment cable 238 may be pulled in a proximal direction through the sheath 240, thus reducing the distance between the posterior side 234 and the anterior side 232.

The posterior side 234 of the inner core 230 has an elongated outwardly-opening circumferential slot 246 which closely receives the expansion insert 244. The expansion insert 244 has a thin arcuate configuration with the central boss 242 extending radially inward as well as a pair of expansion-limiting bosses 248 also extending radially inward from opposite ends. As seen in FIG. 23B, the posterior side 234 also includes a pair of spaced apart short slots 250 through which the expansion-limiting bosses 248 project. The posterior side 234 is bifurcated at its midpoint such that the two abutting ends may be separated from an expansion force, as described above. As the free ends of the posterior side 234 separate, the short slots 250 slide outward over the expansion insert 244 until the expansion-limiting bosses 248 reach the other end of the short slots, which prevents further expansion. Each of the expansion-limiting bosses 248 has a triangular inner end which closely engages an inside of a compression sleeve 252 provided around the expansion joints. The compression sleeve 252 helps prevent premature expansion of the inner core 230 prior to application of a dilatory force such as from a balloon or expanding heart valve.

FIG. 25 is a perspective view of a still further expandable mitral annuloplasty ring inner core 260 having a shape adjustment mechanism and post-implant expansion capability. As before, an adjustment cable 262 extending from the distal end of the sheath 264 extends through an anterior side of the inner core 260 and is secured to an anchor pin 266 on the posterior side. Pulling on the adjustment cable 262 reduces the A-P dimension of the inner core 260.

In addition, an expansion joint similar to that described above with respect to FIGS. 23-24 is provided, including an expansion insert having expansion-limiting bosses 268 extending through inner slots in the core 260. However, the expansion joint is located on the straighter anterior side instead of the posterior side. Again, in this way, it is believed that the final peripheral shape of the initially D-shaped inner core 260 will become more circular, thus better matching the exterior cylindrical shape of an expandable heart valve placed therein, which reduces the possibility of regurgitation therebetween.

Finally, FIG. 26 is a plan view of still further mitral annuloplasty ring inner core 270 adapted for post-implant shape adjustment and expansion. In this configuration, a radial through bore 272 is provided in the anterior side opposite an anchor pin 274 centered in the posterior side. This enables incorporation of the previously-described shape adjustment mechanism of a sheath and adjustment cable.

Additionally, the inner core 270 includes two expansion joints 276, one each centered in a lateral side of the core. The expansion joints 276 will not be described in detail, and may be configured in a variety of manners as described herein. The advantage of placing the expansion joints 276 in the lateral sides of the core is that the core expands into a more circular shape during a valve-in-ring procedure. This helps reduce the size of gaps around the valve and thus increases the chance of zero regurgitation with the use of filler such as fabric and the like.

While the foregoing is a complete description of the preferred examples, various alternatives, modifications, and equivalents may be used. Moreover, it will be obvious that certain other modifications may be practiced within the scope of the appended claims.

What is claimed is:

1. An adjustable annuloplasty ring and delivery system, comprising:

an annuloplasty ring having a continuous peripheral shape around a central aperture, the annuloplasty ring having an inner core formed of an elastic-plastic metal having a yield strength and a suture-permeable interface surrounding the inner core and extending around the peripheral shape;

a delivery system including a flexible sheath coupled to the inner core at a first side of the annuloplasty ring, the sheath housing a flexible cable configured to slide through the sheath, the cable passing through the first side of the annuloplasty ring and extending across the central aperture to a diametrically-opposed second side of the annuloplasty ring, whereby the cable attaches securely to the inner core at the second side; and an actuation mechanism at a proximal handle of the delivery system configured to pull the cable proximally relative to the sheath, and the inner core having cross-sectional dimensions and the yield strength being such that a dimension between the first and second sides is permanently reduced by a predetermined tension on the cable.

2. The adjustable annuloplasty ring and delivery system of claim 1, wherein the annuloplasty ring is shaped for implant at the mitral annulus and the peripheral shape is a rounded D-shape with a relatively straight anterior segment opposite an arcuate posterior segment, with a shorter minor axis extending between the anterior and posterior segments and a longer major axis extending perpendicular to the minor axis and between side segments, and wherein the first side is the anterior segment and the second side is the posterior segment.

3. The adjustable annuloplasty ring and delivery system of claim 2, wherein the inner core has a radial thickness in the anterior segment that is greater than a radial thickness in the posterior segment.

4. The adjustable annuloplasty ring and delivery system of claim 3, wherein the inner core has an axial thickness in the side segments that is greater than axial thicknesses in both the anterior and the posterior segments.

5. The adjustable annuloplasty ring and delivery system of claim 4, wherein the elastic-plastic metal has a yield strength less than about 300 MPa.

6. The adjustable annuloplasty ring and delivery system of claim 5, wherein the elastic-plastic metal is a titanium alloy.

7. The adjustable annuloplasty ring and delivery system of claim 3, wherein the inner core has a rectangular cross-sectional shape.

8. The adjustable annuloplasty ring and delivery system of claim 1, wherein the inner core has at least one expansion joint around the peripheral shape which permits expansion of the inner core upon application of a dilatory force greater than normal physiological forces imparted to the inner core from a surrounding annulus.

9. The adjustable annuloplasty ring and delivery system of claim 1, wherein the sheath and cable form a primary shape adjustment mechanism, and the delivery system further includes a secondary shape adjustment mechanism including a flexible second sheath with a second cable configured to slide through the second sheath, the second cable passing through a third side of the annuloplasty ring and extending across the central aperture to a diametrically-opposed fourth side of the annuloplasty ring, whereby the second cable attaches securely to the ring core at the fourth side, and wherein the first cable and second cable cross the central aperture at about a 90° angle with respect to each other.

10. The adjustable annuloplasty ring and delivery system of claim 1, wherein the inner core has a rectangular cross-sectional shape and is radially thicker in the first side than in the second side, and the peripheral shape is three-dimensional forming a saddle with the first and second sides bowed upward from intermediate segments therebetween, and wherein the inner core is axially thicker in the intermediate segments that it is in the first and second sides.

11. An adjustable annuloplasty ring and delivery system, comprising:

an annuloplasty ring having a continuous peripheral shape around a central aperture, the annuloplasty ring having an inner core formed of an elastic-plastic metal having a yield strength and a suture-permeable interface surrounding the inner core and extending around the peripheral shape, the inner core having at least one expansion joint around the peripheral shape which permits expansion of the inner core upon application of a dilatory force greater than normal physiological forces imparted to the inner core from a surrounding annulus but restricts contraction of the inner core at the expansion joint;

a delivery system including a flexible sheath coupled to the inner core at a first side of the annuloplasty ring, the sheath housing a flexible cable configured to slide through the sheath, the cable extending across the central aperture to a second side of the annuloplasty ring, whereby the cable attaches securely to the inner core at the second side; and an actuation mechanism at a proximal handle of the delivery system configured to pull the cable proximally relative to the sheath, and the inner core having cross-sectional dimensions and the yield strength being such that a dimension between the first and second sides is permanently reduced by a predetermined tension on the cable.

12. The adjustable annuloplasty ring and delivery system of claim 11, wherein the annuloplasty ring is shaped for implant at the mitral annulus and the peripheral shape is a rounded D-shape with a relatively straight anterior segment opposite an arcuate posterior segment, with a shorter minor axis extending between the anterior and posterior segments and a longer major axis extending perpendicular to the minor axis and between side segments, and wherein the first side is the anterior segment and the second side is the posterior segment.

13. The adjustable annuloplasty ring and delivery system of claim 12, wherein the inner core has a radial thickness in the anterior segment that is greater than a radial thickness in the posterior segment.

14. The adjustable annuloplasty ring and delivery system of claim 13, wherein the inner core has an axial thickness in the side segments that is greater than axial thicknesses in both the anterior and the posterior segments.

15. The adjustable annuloplasty ring and delivery system of claim 14, wherein the elastic-plastic metal has a yield strength less than about 300 MPa.

16. The adjustable annuloplasty ring and delivery system of claim 15, wherein the elastic-plastic metal is a titanium alloy.

17. The adjustable annuloplasty ring and delivery system of claim 13, wherein the inner core has a rectangular cross-sectional shape.

18. The adjustable annuloplasty ring and delivery system of claim 12, wherein the expansion joint is centered in the posterior segment.

19. The adjustable annuloplasty ring and delivery system of claim 12, wherein the expansion joint is centered in the anterior segment.

20. The adjustable annuloplasty ring and delivery system of claim 12, wherein there are two of the expansion joints each centered in one of the side segments.

21. The adjustable annuloplasty ring and delivery system of claim 11, wherein the inner core has two expansion joints spaced around the peripheral shape.

22. The adjustable annuloplasty ring and delivery system of claim 11, wherein the sheath and cable form a primary shape adjustment mechanism, and the delivery system further includes a secondary shape adjustment mechanism including a flexible second sheath with a second cable configured to slide through the second sheath, the second cable passing through a third side of the annuloplasty ring and extending across the central aperture to a diametrically-opposed fourth side of the annuloplasty ring, whereby the second cable attaches securely to the ring core at the fourth side, and wherein the first cable and second cable cross the central aperture at a 90° angle with respect to each other.

23. The adjustable annuloplasty ring and delivery system of claim 11, wherein the inner core has a rectangular cross-sectional shape and is radially thicker in the first side than in the second side, and the peripheral shape is three-dimensional forming a saddle with the first and second sides bowed upward from intermediate segments therebetween, and wherein the inner core is axially thicker in the intermediate segments that it is in the first and second sides.

24. The adjustable annuloplasty ring and delivery system of claim 11, wherein the expansion joint comprises two overlapping free ends of the inner core.

25. The adjustable annuloplasty ring and delivery system of claim 11, wherein the expansion joint comprises two abutting free ends of the inner core having circumferential channels in which an expansion insert slides.

26. The adjustable annuloplasty ring and delivery system of claim 11, wherein the expansion joint has a stop which limits a maximum expansion of the inner core.

* * * * *